United States Patent
Krell et al.

(10) Patent No.: US 9,598,376 B2
(45) Date of Patent: Mar. 21, 2017

(54) PREPARATION OF AND FORMULATION COMPRISING A MEK INHIBITOR

(71) Applicants: Novartis AG, Basel (CH); Array BioPharma, Inc., Boulder, CO (US)

(72) Inventors: Christoph Max Krell, Basel (CH); Marian Misun, Basel (CH); Daniel Andreas Niederer, Basel (CH); Werner Heinz Pachinger, Basel (CH); Marie-Christine Wolf, Basel (CH); Daniel Zimmermann, Basel (CH); Weidong Liu, Boulder, CO (US); Peter J. Stengel, Boulder, CO (US); Paul Nichols, Boulder, CO (US)

(73) Assignees: Array BioPharma, Inc., Boulder, CO (US); Novartis AG, Basel (CH)

( * ) Notice: Subject to any disclaimer, the term of this patent is extended or adjusted under 35 U.S.C. 154(b) by 0 days.

(21) Appl. No.: 15/053,441

(22) Filed: Feb. 25, 2016

(65) Prior Publication Data

US 2016/0168104 A1 Jun. 16, 2016

Related U.S. Application Data

(60) Continuation of application No. 14/974,655, filed on Dec. 18, 2015, which is a division of application No. 14/057,498, filed on Oct. 18, 2013, now Pat. No. 9,238,627.

(60) Provisional application No. 61/716,169, filed on Oct. 19, 2012.

(51) Int. Cl.

| | | |
|---|---|---|
| *C07D 235/08* | (2006.01) | |
| *C07D 235/06* | (2006.01) | |
| *A61K 47/26* | (2006.01) | |
| *A61K 47/38* | (2006.01) | |
| *A61K 9/20* | (2006.01) | |
| *C30B 7/08* | (2006.01) | |
| *C30B 29/54* | (2006.01) | |
| *A61K 47/02* | (2006.01) | |
| *A61K 47/12* | (2006.01) | |

(52) U.S. Cl.
CPC .......... *C07D 235/06* (2013.01); *A61K 9/2018* (2013.01); *A61K 47/02* (2013.01); *A61K 47/12* (2013.01); *A61K 47/26* (2013.01); *A61K 47/38* (2013.01); *C07D 235/08* (2013.01); *C30B 7/08* (2013.01); *C30B 29/54* (2013.01); *C07B 2200/13* (2013.01)

(58) Field of Classification Search
None
See application file for complete search history.

(56) References Cited

U.S. PATENT DOCUMENTS

| | | |
|---|---|---|
| 7,235,537 B2 | 6/2007 | Wallace |
| 9,156,795 B2 | 10/2015 | DeMattei |
| 9,238,627 B2 | 1/2016 | Krell et al. |
| 9,382,212 B1 | 7/2016 | Krell et al. |
| 2016/0168103 A1 | 6/2016 | Krell et al. |

FOREIGN PATENT DOCUMENTS

| | | |
|---|---|---|
| WO | WO 03/077914 | 9/2003 |
| WO | WO 2007/002092 | 1/2007 |
| WO | WO 2007/002157 | 1/2007 |

OTHER PUBLICATIONS

Caira, "Crystalline Polymorphism of Organic Compounds," Tops in Current Chemistry, 1998, vol. 198, 163-208.
Supplementary European Search Report in European Application No. 13847106, dated Jun. 6, 2016, 14 pages.
Ascierto et al., "Efficacy and safety of oral MEK162 in patients with locally advanced and unresectable or metastatic cutaneous melanoma harboring BRAFV600 or NRAS mutations," J Clin Oncol, 2012, 30(Suppl): Abstract 8511, retrieved on Aug. 13, 2015, http://meetinglibrary.asco.org/content/93855-114, 5 pages.
Dhillon et al., "MAP kinase signalling pathways in cancer," Oncogene, 2007, 26:3279-3290.
Finn et al., "A phase I study of MEK inhibitor MEK162 (ARRY-438162) in patients with biliary tract cancer," J. Clin Oncol, 2012, 30(Suppl 4): Abstract 220, retrieved on Aug. 13, 2015, http://meetinglibrary.asco.org/content/886534-115, 5 pages.
Fremin and Meloche, "From basic research to clinical development of MEK1/2 inhibitors for cancer therapy," J. Hematol. Oncol., 2010, 3:8, 11 pages.
Haura et al., "A phase II study of PD-0325901, an oral MEK inhibitor, in previously treated patients with advanced non-small cell lung cancer," Clin. Cancer Res., 2010, 16:2450-2457.
International Preliminary Report on Patentability in International Application No. PCT/US2013/065633, dated Apr. 21, 2015, 11 pages.
International Search Report in International Application No. PCT/US2013/065633, dated Mar. 13, 2014, 7 pages.
Murugan et al., "MEK1 mutations, but not ERK2 mutations, occur in melanomas and colon carcinomas, but none in thyroid carcinomas," Cell Cycle, 2009, 8:2122-2124.

(Continued)

*Primary Examiner* — Kamal Saeed
(74) *Attorney, Agent, or Firm* — Fish & Richardson P.C.

(57) ABSTRACT

The present invention relates to processes for preparing 6-(4-bromo-2-fluorophenylamino)-7-fluoro -3-methyl-3H-benzoimidazole-5-carboxylic acid (2-hydroxyethyoxy)-amide, processes for preparing crystallized 6-(4-bromo-2-fluorophenylamino)-7-fluoro-3-methyl-3H-benzoimidazole-5-carboxylic acid (2-hydroxyethyoxy)-amide, and intermediates useful therefore. Also provided herein are pharmaceutical compositions comprising this crystallized compound.

14 Claims, 2 Drawing Sheets

(56) References Cited

OTHER PUBLICATIONS

Paul et al., "N, N1-Carbonyldimidazole, a New Peptide Forming Reagent," JACS, 1960, 82:4596-4600.
Sasaki et al., "MEK1 and AKT2 mutations in Japanese lung cancer," J. Thorac. Oncol., 2010, 5:597-600.
Woodman et al., "N,N1-Carbonyldimidazole-Mediated Amids Coupling: Significant Rate Enhancement Achieved by Acid Catalysis with Imidazole-HCl," Organic Process Research & Development, 2009, 13:106-113.
Written Opinion in International Application No. PCT/US2013/065633, dated Mar. 13, 2014, 10 pages.

PREPARATION OF AND FORMULATION COMPRISING A MEK INHIBITOR

CROSS-REFERENCE TO RELATED APPLICATIONS

This application is a continuation of U.S. application Ser. No. 14/974,655, filed Dec. 18, 2015, which is a divisional application of U.S. application Ser. No. 14/057,498, filed Oct. 18, 2013, which claims priority to U.S. Provisional Application No. 61/716,169, filed Oct. 19, 2012, all of which are incorporated herein by reference in their entireties.

FIELD OF INVENTION

Provided herein are processes for preparing 6-(4-bromo-2-fluorophenylamino)-7-fluoro-3-methyl-3H-benzoimidazole-5-carboxylic acid (2-hydroxyethyoxy)-amide, processes for preparing crystallized 6-(4-bromo-2-fluorophenylamino)-7-fluoro-3-methyl-3H-benzoimidazole-5-carboxylic acid (2-hydroxyethyoxy)-amide, and intermediates useful therefore. Also provided herein are pharmaceutical compositions comprising this crystallized compound.

BACKGROUND

Growth factor-mediated proliferative signals are transmitted from the extracellular environment to the nucleus through several pathways, including the RAS/RAF/MEK pathway. The RAS/RAF/MEK kinase signal transduction pathway is activated through initial extracellular binding and stimulation of tyrosine receptor kinases (RTKs) by their respective cognate ligands. Upon autophosphorylation of specific tyrosine residues in the cytosolic domain of RTKs, the Grb2-Sos complex translocates to the plasma membrane, and converts the inactive RAS•GDP to active RAS•GTP. The interaction between the Grb2 docking protein and the activated kinases or the phosphorylated receptor associated proteins is mediated by the Src Homology (SH2) domain of the signaling protein that recognizes specific phosphotyrosine sequences. RAS undergoes a conformational change upon guanosine 5'-triphosphate (GTP) binding and causes the recruitment of RAF-1 to the cytoplasmic membrane where it is phosphorylated by several kinases and simultaneous disphosphorylated at key residues by protein phosphatase-2B. Activated RAF phosphorylates the mitogen-activated protein kinase kinase (MEK) on two serine residues in the activation loop, which results in the activation of this protein kinase. MEK then phosphorylates and activates extracellular signal-regulated kinase (ERK), allowing its translocation to the nucleus where it phosphorylates transcriptional factors permitting the expression of a variety of genes.

The RAS/RAF/MEK signal transduction pathway is deregulated, often through mutations that result in ectopic protein activation, in roughly ⅓ of human cancers. This deregulation in turn results in a wide array of cellular changes that are integral to the etiology and maintenance of a cancerous phenotype including, but not limited to, the promotion of proliferation and evasion of apoptosis (Dhillon et al., Oncogene, 2007, 26: 3279-3290). Accordingly, the development of small molecule inhibitors of key members of the RAS/RAF/MEK signal transduction pathway has been the subject of intense effort within the pharmaceutical industry and oncology community.

MEK is a major protein in the RAS/RAF/MEK pathway, which signals toward cell proliferation and survival, and frequently activated in tumors that have mutations in the RAS or RAF oncogenes or in growth receptor tyrosine kinases. MEK is a key player in the RAS/RAF/MEK pathway as it is downstream of RAS and RAF. Despite being only rarely mutated in cancer (Murugan et al., Cell Cycle, 2009, 8: 2122-2124; Sasaki et al., J. Thorac. Oncol., 2010, 5: 597-600), inhibitors of the MEK1 and MEK2 proteins have also been targeted for small molecule inhibition owing to their central position within the RAS/RAF/MEK signal transduction pathway signaling cascade (Fremin and Meloche, J. Hematol. Oncol., 2010, 3:8). Recently a potent MEK inhibitor failed to demonstrate efficacy in clinical trials in patients with advanced non-small cell lung cancer (Haura et al., Clin. Cancer Res., 2010, 16: 2450-2457). The reason for failure in this trial is not clear.

6-(4-Bromo-2-fluorophenylamino)-7-fluoro-3-methyl-3H-benzoimidazole-5-carboxylic acid (2-hydroxyethyoxy)-amide (hereinafter, "Compound A") is a benzimidazole compound that is a known potent and selective inhibitor of the MEK1 and MEK2 proteins, and useful in the treatment of hyperproliferative diseases, particularly cancer, in mammals. For example, in a recently published Phase I study of 28 patients suffering from unresectable, locally advanced or metastatic biliary cancer and who had received ≤1 prior systemic therapy, oral Compound A treatment (60 mg twice daily) resulted in 1 complete regression, 1 partial regression and 11 stable disease diagnoses after at least 6 weeks of treatment (Finn et al., J. Clin. Oncol. 30, 2012 (Supplement 4, 2012 Gastrointestinal Cancers Symposium, Abstract No. 220). Compound A has also been demonstrated to be effective in the treatment of patients with either BRAFV600 or NRAS-mutant melanoma (Ascierto et al., J. Clin. Oncol. 30, 2012 (Supplement, 2012 ASCO Annual Meeting, Abstract No. 8511).

The compound, as well as a process for its preparation, is disclosed in PCT Pub. No. WO 03/077914. The manufacturing process for preparing Compound A is described in Example 18 of this document. The manufacturing process described therein are, although suitable, regarded as disadvantageous for commercial production.

Due to the high potency of this benzimidazole compound, in particular as MEK inhibitor, there is a need for improved manufacturing methods of such compounds. In particular, there is a need to provide processes that fulfill one or more of the following criteria: scalable, safer, simpler, higher yielding and more economical when compared to known processes.

There also remains a need for new solid forms for the treatment of cancer.

The present invention is directed to an improved process for the production of Compound A that is suitable for small scale or large scale manufacture, and useful intermediates thereof. The present invention is further directed to a process for the production of crystallized Compound A as well as a new pharmaceutical composition suitable for administration of this crystallized compound. It has been surprisingly discovered that crystallized Compound A prepared according to the inventive processes has an improved purity profile and an improved physical morphology which is advantageous in pharmaceutical drug development and manufacture.

SUMMARY OF THE INVENTION

Provided herein are processes for preparing 6-(4-bromo-2-fluorophenylamino)-7-fluoro-3-methyl-3H-benzoimidazole-5-carboxylic acid (2-hydroxyethyoxy)-amide, processes for preparing crystallized 6-(4-bromo-2-fluorophenylamino)-7-fluoro-3-methyl-3H-benzoimidazole-5-carboxylic acid (2-hydroxyethyoxy)-amide, and intermediates useful therefore. Also provided herein are pharmaceutical compositions comprising this crystallized compound.

In one aspect, provided herein is a process for preparing a compound 6-(4-bromo-2-fluorophenylamino)-7-fluoro-3-methyl-3H-benzoimidazole-5-carboxylic acid (2-hydroxyethyoxy)-amide (herein referred to as "Compound A"):

Compound A

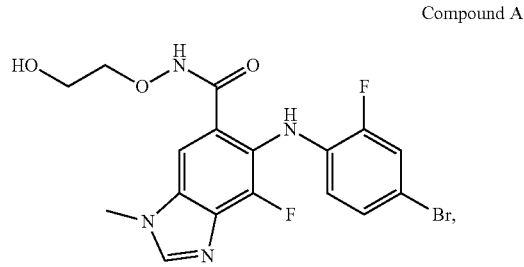 [SMILES: Cn1cnc2c(F)c(Nc3ccc(Br)cc3F)c(C(=O)NOCCO)cc21]

wherein the process comprising the steps of:
a) reacting a compound of Formula (I):

Formula (I)

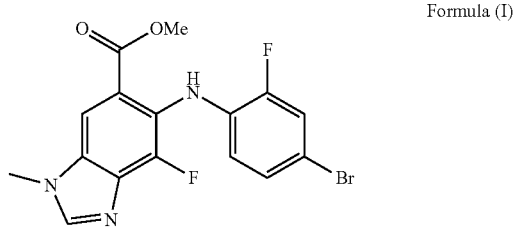 [SMILES: COC(=O)c1cc2c(ncn2C)c(F)c1Nc1ccc(Br)cc1F]

with a suitable base to form an intermediate; and
b) reacting said intermediate with a compound of Formula (II):

Formula (II)

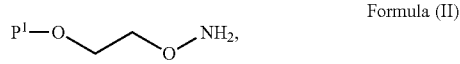

to provide a compound of Formula (III):

Formula (III)

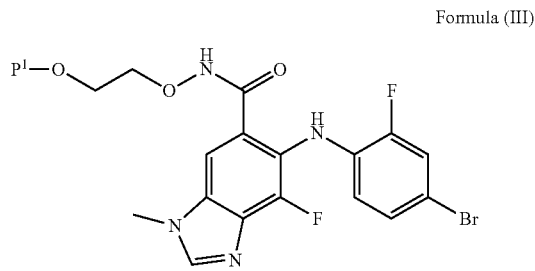

or a hydrate thereof,
wherein $P^1$ is a protecting group;

c) dissolving said compound of Formula (III) or a hydrate thereof in a suitable solvent or solvent system; and
d) deprotecting said compound of Formula (III) or a hydrate thereof with a suitable deprotecting reagent,
wherein $P^1$ in each occurrence may be the same or different, and is a suitable protecting group, to provide Compound A.

In another aspect, provided herein is a process for preparing a compound of Formula (III):

Formula (III)

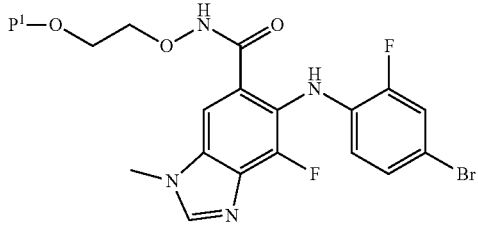

or a hydrate thereof, wherein the process includes the steps of:
a) reacting a compound of Formula (I):

Formula (I)

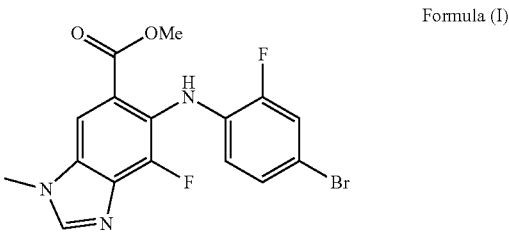 [SMILES: COC(=O)c1cc2c(ncn2C)c(F)c1Nc1ccc(Br)cc1F]

with a suitable base to form an intermediate; and
b) reacting the intermediate with a compound of Formula (II):

Formula (II)

wherein $P^1$ is a protecting group, such that the compound of Formula (III) or a hydrate thereof is formed.

In certain embodiments of both processes, steps a) and b) are carried out as a "one-pot" synthesis, wherein the intermediate of step a) is reacted with the compound of Formula (II) without first being isolated from the reaction mixture of step a). In one particular embodiment, step a) comprises reacting the compound of Formula (I) with the suitable base to form Intermediate 1 (structure shown below), and step b) comprises reacting Intermediate 1 with the compound of Formula (II) to form the compound of Formula (III), or a hydrate thereof. In one embodiment, Intermediate 1 is not isolated from the reaction mixture of step a) prior to step b). In another embodiment, Intermediate 1 is part of a solution comprising solvents selected from the group consisting of DMF and THF.

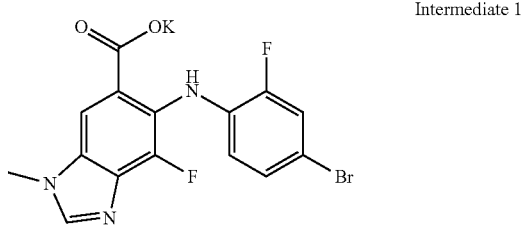

Intermediate 1

In contrast, in other embodiments, the intermediate formed in step a) is isolated from the reaction mixture before reacting with the compound of Formula (II). In one embodiment, step a) comprises reacting the compound of Formula (I) with the suitable base to form an intermediate of Formula (V) (structure shown below), and isolating the intermediate from the reaction mixture; and step b) comprises reacting the intermediate of Formula (V) with the compound of Formula (II) to form the compound of Formula (III), or a hydrate thereof. As such, in this embodiment, steps a) and b) are not carried out as a "one-pot" procedure but as separate production steps wherein the intermediate of step a) is isolated before reaction with the compound of Formula (II) in step b). In one particular embodiment, step a) comprises reacting the compound of Formula (I) with the suitable base followed by reacting with an acid to form an intermediate of Formula (V), and isolating the intermediate from the reaction mixture; and step b) comprises reacting the intermediate of Formula (V) with the compound of Formula (II) to form the compound of Formula (III), or a hydrate thereof. In one embodiment of the process, step a) comprises crystalizing and collecting the intermediate from the reaction mixture. In one embodiment, the intermediate is crystalized and collected by filtration. This additional isolation step can be advantageous as it removes starting materials and process impurities prior to the coupling reaction with the compound of Formula (II). In certain embodiments of the processes, isolating the intermediate of step a) improves synthesis yields.

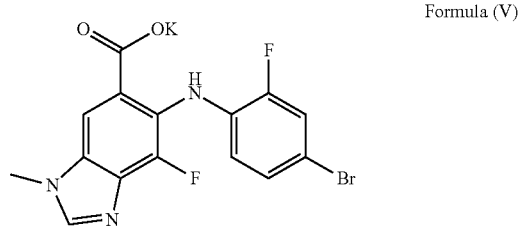

Formula (V)

In another aspect, there is provided a process for preparing a crystallized form of Compound A:

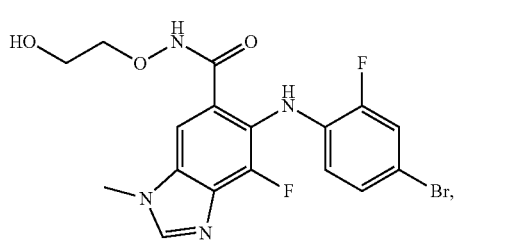

Compound A the process including the steps of:

a) dissolving Compound A in a solution comprising (i.) a solvent system comprising an ether and optionally an alcohol, and (ii.) water to provide a solution;

b) adding a seed crystal suspension to the solution to provide a suspension mixture;

d) adding water to the suspension mixture to provide a treated mixture; and e) cooling the treated mixture, to provide the crystallized 6-(4-bromo-2-fluorophenylamino)-7-fluoro-3-methyl-3H-benzoimidazole-5-carboxylic acid (2-hydroxyethyoxy)-amide.

In another aspect, there is provided a process for preparing a crystallized form of Compound A:

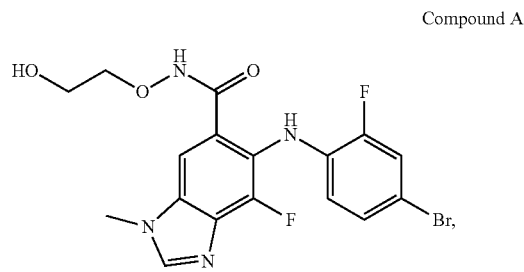 [SMILES: Cn1cnc2c(F)c(Nc3ccc(Br)cc3F)c(C(=O)NOCCO)cc21]

Compound A the process including the steps of:

a) dissolving Compound A in a solution comprising (i.) a solvent system comprising an ether and optionally an alcohol, and (ii.) water to provide a solution;

b) adding a seed crystal suspension to the solution to provide a suspension mixture;

c) cooling the suspension mixture to provide a cooled suspension mixture;

d) adding water to the cooled suspension mixture to provide a treated mixture; and e) cooling the treated mixture, to provide the crystallized 6-(4-bromo-2-fluorophenylamino)-7-fluoro-3-methyl-3H-benzoimidazole-5-carboxylic acid (2-hydroxyethyoxy)-amide.

In another aspect, there is provided a crystallized 6-(4-bromo-2-fluorophenylamino)-7-fluoro-3-methyl-3H-benzoimidazole-5-carboxylic acid (2-hydroxyethyoxy)-amide prepared in accordance with the process described herein.

In another aspect, there is provided a compound of formula (I):

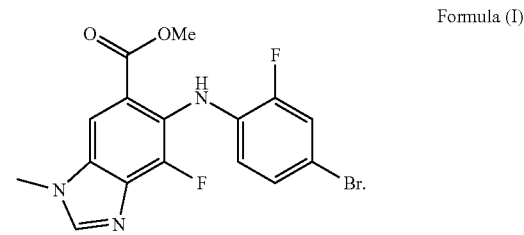 [SMILES: COC(=O)c1cc2c(ncn2C)c(F)c1Nc1ccc(Br)cc1F]

Formula (I)

Said compound of formula (I) is useful as an intermediate compound for the synthesis of Compound A in accordance with the present invention.

In another aspect, provided herein is a compound of formula (V):

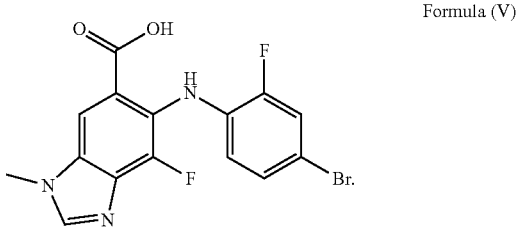 [SMILES: Cn1cnc2c(F)c(Nc3ccc(Br)cc3F)c(C(=O)O)cc21]

Formula (V)

Said compound of Formula (V) is useful as an intermediate compound for the synthesis of Compound A in accordance with the present invention.

In another aspect, there is provided a compound of formula (IV):

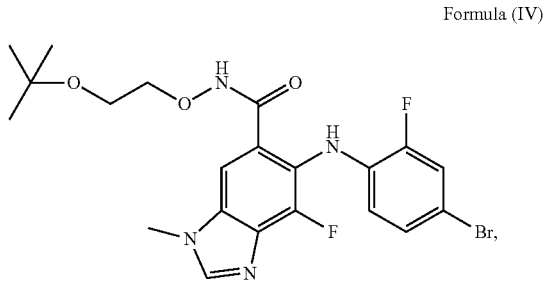 [SMILES: Cn1cnc2c(F)c(Nc3ccc(Br)cc3F)c(C(=O)NOCCOC(C)(C)C)cc21]

Formula (IV)

or a hydrate thereof. In a preferred embodiment, the compound of formula (IV) is in the form of its monohydrate. Said compound of formula (IV), including the monohydrate, is useful as an intermediate compound for the synthesis of Compound A in accordance with the present invention.

In another aspect, there is provided a pharmaceutical composition comprising crystallized 6-(4-bromo-2-fluorophenylamino)-7-fluoro-3-methyl-3H-benzoimidazole-5-carboxylic acid (2-hydroxyethyoxy)-amide, at least one sugar, and at least one cellulose-derivative excipient.

In another aspect, there is provided a method of treating a proliferative disease, particularly cancer, in a subject, comprising administering to the subject in need thereof the pharmaceutical composition comprising crystallized 6-(4-bromo-2-fluorophenylamino)-7-fluoro-3-methyl-3H-benzoimidazole-5-carboxylic acid (2-hydroxyethyoxy)-amide, at least one sugar, and at least one cellulose-derivative excipient.

DETAILED DESCRIPTION OF THE FIGURES

DETAILED DESCRIPTION OF THE INVENTION

Figure 1:
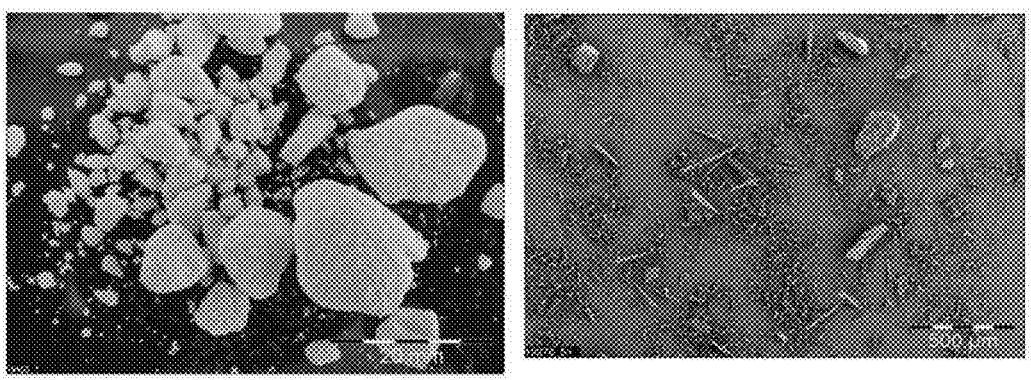
FIG. 1 shows two microscopy images of the agglomerated drug substance Compound A produced by prior processes.

Provided herein are processes useful for the preparation and synthesis of a potent and selective MEK ½ inhibitor 6-(4-Bromo-2-fluorophenylamino)-7-fluoro-3-methyl-3H-benzoimidazole-5-carboxylic acid (2-hydroxyethyoxy)-amide ("Compound A"), and useful intermediates thereof.

The present invention is further directed to a process for the synthesis of crystallized Compound A as well as a pharmaceutical composition suitable for administration of this crystallized compound.

These processes are advantageous over previously known processes (e.g., WO 03/077914) in several ways. For example, the instant processes for the formation of Compound A have an improved purity profile with low levels (less than 1 ppm) of palladium.

The general terms used herein are defined with the following meanings, unless explicitly stated otherwise.

"Subject" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

The terms "effective amount" or "pharmaceutically effective amount" or "therapeutically effective amount" refer to a sufficient amount of an agent to provide the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In reference to cancer, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations. The effective amount of the drug or composition may: (i) reduce the number of cancer cells; (ii) reduce tumor size; (iii) inhibit, retard, slow to some extent, and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Unless otherwise indicated, "treating" or "treatment" of a disease, disorder, or syndrome, as used herein, means inhibiting the disease, disorder, or syndrome, that is, arresting its development; and relieving the disease, disorder, or syndrome, that is, causing regression of the disease, disorder, or syndrome. As is known in the art, in the context of treatment, adjustments for systemic versus localized delivery, age, body weight, general health, sex, diet, time of administration, drug interaction and the severity of the condition may be necessary, and will be ascertainable with routine experimentation by one of ordinary skill in the art.

"Prevention" means preventing the disease, disorder, or syndrome from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome.

"Pharmaceutical composition" means a mixture or solution containing at least one therapeutic agent to be administered to a subject, e.g., a mammal or human, in order to prevent or treat a particular disease or condition affecting the mammal.

"Pharmaceutically acceptable" means those compounds, materials, compositions and/or dosage forms, which are, within the scope of sound medical judgment, suitable for contact with the tissues a subject, e.g., a mammal or human, without excessive toxicity, irritation allergic response and other problem complications commensurate with a reasonable benefit/risk ratio.

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

As used herein, the terms "approximately" or "about" generally indicate a possible variation of no more than 10%, 5%, or 1% of a value.

As used herein, the term "isolated" is meant that a compound is separated from the reaction mixture in which it is formed or detected. An isolated compound comprises less than 15%, less than 10%, less than 6%, or less than 3% by weight of organic solvents or water. Non-limited examples of the separation methods include filtration, centrifugation, vacuum drying, precipitation, crystallization, and column chromatography.

In one aspect, provided herein is a process for preparing a compound 6-(4-bromo-2-fluorophenylamino)-7-fluoro-3-methyl-3H-benzoimidazole-5-carboxylic acid (2-hydroxyethyoxy)-amide (herein referred to as "Compound A")

Compound A

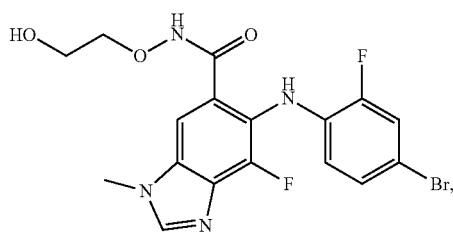

wherein the process comprising the steps of:
a) reacting a compound of Formula (I):

Formula (I)

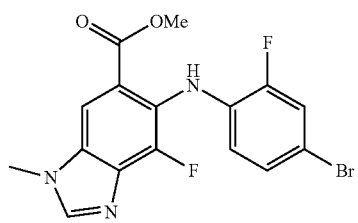

with a suitable base to form an intermediate; and
b) reacting said intermediate with a compound of Formula (II):

Formula (II)

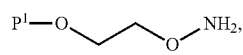

to provide a compound of Formula (III):

Formula (III)

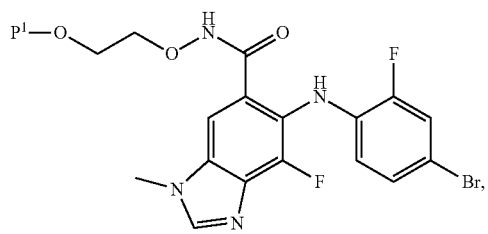

or a hydrate thereof,
wherein $P^1$ is a protecting group;
c) dissolving said compound of Formula (III) or a hydrate thereof in a suitable solvent or solvent system; and
d) deprotecting said compound of Formula (III) or a hydrate thereof with a suitable deprotecting reagent,
wherein $P^1$ in each occurrence may be the same or different, and is a suitable protecting group, to provide Compound A.

In the process of step a), the compound of Formula (I) is reacted with a suitable base to produce an intermediate. Examples of suitable bases for the foregoing reaction include, but are not limited to, sodium hydroxide, potassium hydroxide, caesium hydroxide, lithium hydroxide, potassium trimethylsilanolate, lithium trimethylsilanolate, and sodium trimethylsilanolate. In a preferred embodiment, the suitable base is potassium trimethylsilanolate. In another preferred embodiment, the suitable base is sodium hydroxide.

The process of step a), in which a compound of Formula (I) is reacted with a suitable base, may be performed in any suitable solvent or solvent system. Suitable solvents include polar aprotic solvents such as acetone, acetonitrile, N,N-dimethylformamide, dimethylsulfoxide, ethyl acetate, tetrahydrofuran, 2-methyl-tetrahydrofuran, and 1,4-dioxane. Suitable solvent systems include any combination of suitable solvents. In a preferred embodiment, the reaction is performed in a mixture of N,N-dimethylformamide and THF. Suitable solvent systems can also include one or more suitable solvents in combination with water. In one particular embodiment, the reaction is performed in a mixture of N,N-dimethylformamide and water.

In one embodiment of the process described above, steps a) and b) are carried out as a "one-pot" synthesis, wherein the intermediate of step a) is reacted with the compound of Formula (II) without first being isolated from the reaction mixture of step a) (see, e.g., Example 2A). In one embodiment, the intermediate of step a) is Intermediate 1:

Intermediate 1

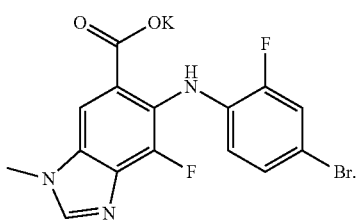

In one particular embodiment of the process comprising the "one-pot" synthesis, step a) comprises reacting the compound of Formula (I) with the suitable base to form Intermediate 1, and step b) comprises reacting Intermediate 1 with the compound of Formula (II) to form the compound of Formula (III), or a hydrate thereof. In one embodiment, Intermediate 1 is not isolated from the reaction mixture of step a) prior to step b). In another embodiment, Intermediate 1 is part of a solution comprising solvents selected from the group consisting of DMF and THF.

In another embodiment of the process, steps a) and b) are carried out with isolation of the intermediate of step a) from the reaction mixture prior to reacting with the compound of Formula (II). In one embodiment, the intermediate of step a) is a compound of Formula (V):

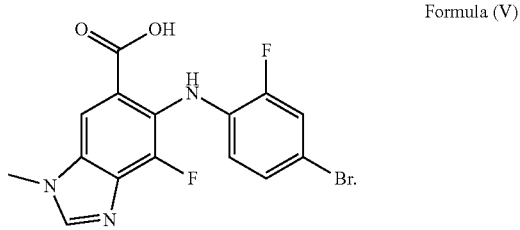 [SMILES: Cn1cnc2c(F)c(Nc3ccc(Br)cc3F)c(C(=O)O)cc21]

Formula (V)

In another embodiment of the process wherein the intermediate of step a) is isolated from the reaction mixture of step a) prior to the reaction of step b), the process comprises isolating the intermediate (e.g., the compound of Formula (V)) from the reaction mixture of step a) prior to step b). In one embodiment, the isolation process comprises crystallizing and collecting the intermediate (e.g., the compound of Formula (V)) from the reaction mixture of step a) prior to step b). In an embodiment, the intermediate is crystallized and collected by filtration.

In another embodiment, step a) comprises reacting the compound of Formula (I) with the suitable base to form an intermediate of Formula (V), and isolating the intermediate from the reaction mixture; and step b) comprises reacting the intermediate of Formula (V) with the compound of Formula (II) to form the compound of Formula (III), or a hydrate thereof. In one particular embodiment of the process wherein the intermediate of step a) is isolated from the reaction mixture of step a) prior to the reaction of step b), step a) comprises reacting the compound of Formula (I) with the suitable base followed by reacting with an acid to form the intermediate of Formula (V), and isolating the intermediate of Formula (V) from the reaction mixture; and step b) comprises reacting the intermediate of Formula (V) with the compound of Formula (II) to form the compound of Formula (III), or a hydrate thereof. In one embodiment, the acid is hydrochloric acid. In another embodiment, step a) of the process comprises crystalizing and collecting the intermediate of Formula (V) from the reaction mixture of step a). In one embodiment, the intermediate is crystalized and collected by filtration.

As used herein, the term "protecting group" is intended to refer to those groups used to prevent reactive groups (such as carboxy, amino, hydroxy, and mercapto groups) from undergoing undesired reactions. In particular, suitable protecting groups for $P^1$ as used throughout the application include acid-labile protecting groups. Illustrative examples of suitable acid-labile protecting groups for $P^1$ as used throughout the application include, but are not limited to: alkyl groups, such as tertiary alkyls (e.g., tertiary $C_4$-$C_7$ alkyls such as t-butyl or tertiary amyl); alkenyl groups; tertiary aryl-alkyl groups, such as 1-methyl-1-phenylethyl (cumyl) or triphenylmethyl (trityl); groups that result in acetals, such as methoxymethyl, 1-ethoxyethyl, 2-tetrahydropyranyl or 2-tetrahydrofuranyl; and silyl groups, such as trimethylsilyl, triethylsilyl or tert-butyl-dimethyldilyl. In a preferred embodiment, $P^1$ is t-butyl.

The process of step b), in which the intermediate from step a) is reacted with a compound of Formula (II), may be performed in the presence of any coupling agent and a proton source. Suitable proton sources include, but are not limited to, imidazole hydrochloride, pyridinium hydrochloride, triethylamine hydrochloride, N-methylmorpholine hydrochloride, and sulfonic acids such as e.g., methanesulfonic acid, and preferably imidazole hydrochloride. Suitable coupling agents include, but are not limited to 1,1'-carbonyldiimidazole, isobutylchloroformate, pivaloyl chloride, oxalyl chloride, thionyl chloride, 1-propanephosphonic acid cyclic anhydride, and 1-(3-dimethylaminopropyl)-3-ethyl-carbodiimide hydrochloride (EDCI), and preferably 1,1'-carbonyldiimidazole. In the preferred embodiment of the present invention, the process of step b) is performed in the presence of the coupling agent 1,1'-carbonyldiimidazole and the proton source imidazole hydrochloride. It is within the knowledge of one of ordinary skill in the art to optimize the process of the present invention for coupling agents other than 1,1'-carbonyldiimidazole and proton sources other than imidazole hydrochloride.

The process of step c), in which the compound of Formula (III) or a hydrate thereof is dissolved in a suitable solvent or solvent system and deprotected, may be performed in any suitable solvent or solvent system. Examples of suitable solvents include (a) polar protic solvents such as methanol, ethanol, and isopropanol, and (b) polar aprotic solvents such as acetone, acetonitrile, N,N-dimethylformamide, dimethylsulfoxide, ethyl acetate, and tetrahydrofuran. Suitable solvent systems include any combination of suitable solvents.

In one embodiment, the reaction is performed in a polar aprotic solvent. In a preferred embodiment, the reaction is performed in acetonitrile.

The protecting group for $P^1$ may be removed using any suitable deprotecting agent. Deprotection conditions for hydroxy protecting groups will necessarily vary with the choice of protecting group. Alkyl groups or alkeynyl groups may be removed, for example, with an aqueous acid, such as phosphoric acid. Tertiary aryl-alkyl groups may be removed, for example, by aqueous acid. Silyl groups may be removed, for example, by fluoride or by aqueous acid. It would be understood by one of ordinary skill that acid-labile protecting groups may be removed with an aqueous acid. Suitable deprotection agents for those protecting groups illustrated above may include, but are not limited to, an aqueous acid such as phosphoric acid, hydrochloric acid or sulfuric acid; non-aqueous acids such as hydrogen chloride acid in isopropyl alcohol or other suitable organic solvents such as 1,4-dioxane or tetrahydrofuran, trimethylsilylchloride, trifluoroacetic acid or p-Toluenesulfonic acid.

In one embodiment, when protecting group $P^1$ is t-butyl, a suitable deprotection agent may be selected from an aqueous acid such as phosphoric acid, hydrochloric acid or sulfuric acid; 5 M hydrochloric acid in isopropyl alcohol, trimethylsilylchloride, or p-Toluenesulfonic acid (hydrate). Preferably, when protecting group $P^1$ is t-butyl, the suitable deprotection agent is aqueous phosphoric acid.

In one embodiment, when the protecting group $P^1$ is t-butyl, the suitable solvent or solvent system in step c) is selected from acetonitrile, tetrahydrofuran, methanol and ethanol, and the deprotection agent is phosphoric acid.

In a further embodiment, when the protecting group P¹ is t-butyl, the suitable solvent or solvent system in step c) is selected from acetonitrile, tetrahydrofuran, methanol, and ethanol, and the deprotection agent is hydrochloric acid.

In a further embodiment of this aspect of the invention, step d) is followed by Compound A provided in step d) may be further converted into any pharmaceutically acceptable salt thereof. A "pharmaceutically acceptable salt", as used herein, unless otherwise indicated, includes salts of acidic and basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of the present invention are those that form non-toxic acid addition salts, i.e., salts containing pharmaceutically acceptable anions, such as the acetate, benzoate, bromide, chloride, citrate, fumarate, hydrobromide, hydrochloride, iodide, lactate, maleate, mandelate, nitrate, oxalate, salicylate, succinate, and tartrate salts. Since a single compound of the present invention may include more than one acidic or basic moieties, the compounds of the present invention may include mono, di or tri-salts in a single compound.

In the case of an acidic moiety in a compound of the present invention, a salt may be formed by treatment of a compound of the present invention with a basic compound, particularly an inorganic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzyl-ethylenediamine, and the like salts. Other salts of acidic moieties may include, for example, those salts formed with procaine, quinine and N-methylglusoamine, plus salts formed with basic amino acids such as glycine, ornithine, histidine, phenylglycine, lysine and arginine. An especially preferred salt is a sodium or potassium salt of a compound of the present invention.

With respect to basic moieties, a salt is formed by the treatment of a compound of the present invention with an acidic compound, particularly an inorganic acid. Preferred inorganic salts of this type may include, for example, the hydrochloric, hydrobromic, sulfuric, phosphoric or the like salts. Preferred organic salts of this type, may include, for example, salts formed with cetic, succinic, citric, maleic, fumaric, D-glutamic, glycolic, benzoic, cinnamic and the like organic acids. An especially preferred salt of this type is a hydrochloride or sulfate salt of Compound A.

It is understood that, in accordance with the present invention, a base may be added to the acidic reaction mixture formed in deprotection step d) to reach a pH in the range of 5-9. Preferably, a base is added to neutralize the acidic reaction mixture formed in deprotection step d) to pH=approximately 8-8.5. Examples of suitable bases include, but are not limited to, potassium hydroxide, sodium hydroxide, lithium hydroxide and ammonium hydroxide. Preferably, the additional base is potassium hydroxide.

In a preferred embodiment, the suitable base in step a) is potassium trimethylsilanolate, the protecting group P¹ is t-butyl, the suitable solvent or solvent system of step c) is acetonitrile, and the suitable deprotection agent in step d) is aqueous phosphoric acid.

In another preferred embodiment, the suitable base in step a) is sodium hydroxide, the protecting group P¹ is t-butyl, the suitable solvent or solvent system of step c) is acetonitrile, and the suitable deprotection agent in step d) is aqueous phosphoric acid.

In another preferred embodiment, the suitable base in step a) is potassium trimethylsilanolate, the protecting group P¹ is t-butyl, the suitable solvent or solvent system of step c) is acetonitrile, the suitable deprotection agent in step d) is phosphoric acid, and a further base is added, wherein the further base is potassium hydroxide.

In still another preferred embodiment, the suitable base in step a) is sodium hydroxide, the protecting group P¹ is t-butyl, the suitable solvent or solvent system of step c) is acetonitrile, the suitable deprotection agent in step d) is phosphoric acid, and a further base is added, wherein the further base is potassium hydroxide.

In another aspect, provided herein is a process for preparing a compound of Formula (III), Formula (III)

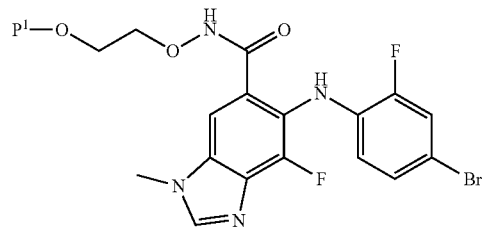

or a hydrate thereof, wherein the process includes the steps of:

a) reacting a compound of Formula (I):

Formula (I)

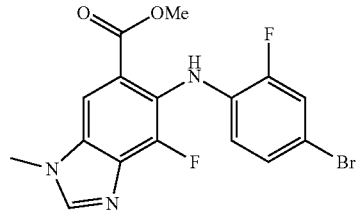

with a suitable base to form an intermediate; and b) reacting said intermediate with a compound of Formula (II):

Formula (II)

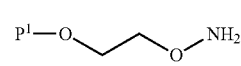

wherein P¹ is a protecting group, such that the compound of Formula (III) or a hydrate thereof is formed.

The process of step a), in which the compound of Formula (I) is reacted with a suitable base to produce an intermediate. Examples of suitable bases for the foregoing reaction include, but are not limited to, sodium hydroxide, potassium hydroxide, caesium hydroxide, lithium hydroxide, potassium trimethylsilanolate, lithium trimethylsilanolate, and sodium trimethylsilanolate. In a preferred embodiment, the suitable base is potassium trimethylsilanolate. In another preferred embodiment, the suitable base is sodium hydroxide.

The process of step a), in which a compound of Formula (I) is reacted with a suitable base, may be performed in any suitable solvent or solvent system. Suitable solvents include polar aprotic solvents such as acetone, acetonitrile, N,N-dimethylformamide, dimethylsulfoxide, ethyl acetate, tetrahydrofuran, 2-methyl-tetrahydrofuran, and 1,4-dioxane. Suitable solvent systems include any combination of suitable solvents. In a preferred embodiment, the reaction is performed in a mixture of N,N-dimethylformamide and THF. Suitable solvent systems can also include one or more suitable solvents in combination with water. In one particular embodiment, the reaction is performed in a mixture of N,N-dimethylformamide and water.

In one embodiment of the process, steps a) and b) are carried out as a "one-pot" synthesis as described above. In one embodiment, the intermediate of step a) is Intermediate 1. In another embodiment, step a) comprises reacting the compound of Formula (I) with the suitable base to form Intermediate 1, and step b) comprises reacting Intermediate 1 with the compound of Formula (II) to form the compound of Formula (III), or a hydrate thereof. In one embodiment, Intermediate 1 is not isolated from the reaction mixture of step a) prior to step b). In another embodiment, Intermediate 1 is part of a solution comprising solvents selected from the group consisting of DMF and THF.

In another embodiment of the process, steps a) and b) are carried out with isolation of the intermediate of step a) prior to the reaction of step b) as described above. In one embodiment, the intermediate of step a) is a compound of Formula (V). In another embodiment, the process comprises isolating the intermediate (e.g., the compound of Formula (V)) from the reaction mixture of step a) prior to step b). In one embodiment, the isolation process comprises crystallizing and collecting the intermediate (e.g., the compound of Formula (V)) from the reaction mixture of step a) prior to step b). In one embodiment, the intermediate is crystallized and collected by filtration.

In another embodiment of the process wherein the intermediate of step a) is isolated from the reaction mixture of step a) prior to the reaction of step b), step a) comprises reacting the compound of Formula (I) with the suitable base to form an intermediate of Formula (V), and isolating the intermediate from the reaction mixture; and step b) comprises reacting the intermediate of Formula (V) with the compound of Formula (II) to form the compound of Formula (III), or a hydrate thereof. In one particular embodiment, step a) comprises reacting the compound of Formula (I) with the suitable base followed by reacting with an acid to form the intermediate of Formula (V), and isolating the intermediate of Formula (V) from the reaction mixture; and step b) comprises reacting the intermediate of Formula (V) with the compound of Formula (II) to form the compound of Formula (III), or a hydrate thereof. In one embodiment, the acid is hydrochloric acid.

Examples of suitable protecting groups $P^1$ include those disclosed above, wherein the text is hereby incorporated by reference in its entirety.

The process of step b), in which the intermediate from step a) is reacted with a compound of Formula (II), may be performed in the presence of any coupling agent and a proton source. Suitable proton sources include, but are not limited to, imidazole hydrochloride, pyridinium hydrochloride, triethylamine hydrochloride, N-methylmorpholine hydrochloride, and sulfonic acids such as e.g., methanesulfonic acid, and preferably imidazole hydrochloride. Suitable coupling agents include, but are not limited to 1,1'-carbonyldiimidazole, isobutylchloroformate, pivaloyl chloride, oxalyl chloride, thionyl chloride, 1-propanephosphonic acid cyclic anhydride, and 1-(3-dimethylaminopropyl)-3-ethyl-carbodiimide hydrochloride (EDCI), and preferably 1-1'-carbonyldiimidazole. In the preferred embodiment of the present invention, the process of step b) is performed in the presence of the coupling agent 1,1'-carbonyldiimidazole and the proton source imidazole hydrochloride. It is within the knowledge of one of ordinary skill in the art to optimize the process of the present invention for coupling agents other than 1,1'-carbonyldiimidazole and proton sources other than imidazole hydrochloride.

In another aspect of the invention, a new process for preparing a new crystallized form of Compound A has been discovered. Prior synthesis processes of Compound A or pharmaceutically acceptable salts thereof, e.g., those in WO03/077914, have been demonstrated to possess the following key disadvantages for pharmaceutical drug development: (a) the synthesized drug substance typically formed big lumps (agglomerates) of powder, (b) insufficient purity profile and yield, and (c) the synthesized drug substance had a "sticky" morphology with poor flowability. Prior processes would produce highly agglomerated material of Compound A which would build lumps, with some having a diameter up to 15 mm. These issues are significant issues that hinder the reliable, repeatable, and controlled large-scale production of pharmaceutical compositions comprising Compound A or pharmaceutically acceptable salts thereof.

A new process for preparing a crystallized form of Compound A has been discovered that surprisingly produces a crystalline form of Compound A having significantly improved purity profile and improved physical morphology (e.g., reduction of sticky crystals/particles, improved flowability). Compound A has been found to have very low solubility in most standard solvents (i.e., less than 1% at room temperature). Due to this low solubility, it is difficult to perform crystallization by standard cooling methods and to control crystal growth. However, it has been discovered that water, which is in general an anti-solvent (solubility <0.01% at a broad temperature range, also unexpectedly acts as a solvent for Compound A when used in a novel solvent mixture comprising an ether and optionally an alcohol, and thus significantly increases the solubility for Compound A. While a small additional of anti-solvent to the solvent can typically slightly increase solubility, the addition of water to a solvent mixture of tetrahydrofuran and methanol increased the solubility of Compound A by approximately 50% compared to the solvent mixture of methanol and tetrahydrofuran without water. This improvement in solubility contributes to an improvement in the purity profile of the final drug substance.

Figure 2:
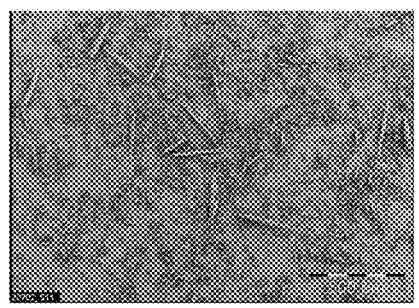
FIG. 2 shows a microscopy image of the crystalline Compound A produced by the new crystallization process of the present invention: (a) without milling, (b) with jet-milling, and (c) with pin-milling.
Figure 2:
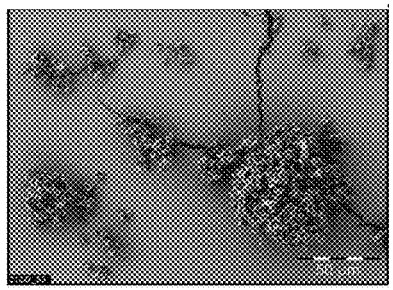
Figure 2:
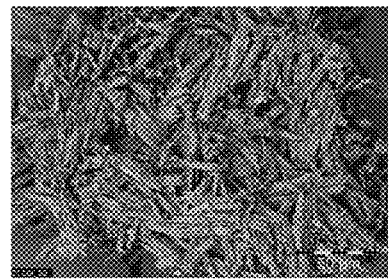

In addition, the new process for preparing a crystallized form of Compound A produces a new crystalline form of Compound A with reduced sticky behavior and improved flowability. This improvement is demonstrated with or without a subsequent milling step as discussed below. (See, FIG. 1 as compared to FIG. 2). The additional milling step, however, provides an advantageous further improvement to the sticky behavior and flowability of Compound A.

Thus, in one aspect, there is provided a process for preparing a crystallized form of Compound A:

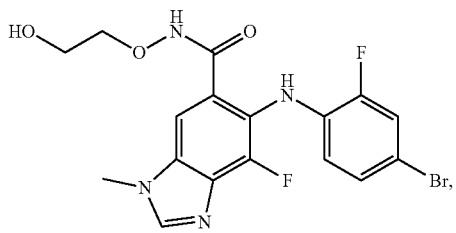

Compound A the process including the steps of:

a) dissolving Compound A in a solution comprising (i.) a solvent system comprising an ether and optionally an alcohol, and (ii.) water to provide a solution;

b) adding a seed crystal suspension to the solution to provide a suspension mixture;

d) adding water to the suspension mixture to provide a treated mixture; and e) cooling the treated mixture, to provide the crystallized 6-(4-bromo-2-fluorophenylamino)-7-fluoro-3-methyl-3H-benzoimidazole-5-carboxylic acid (2-hydroxyethyoxy)-amide.

In another aspect, there is provided a process for preparing a crystallized form of Compound A:

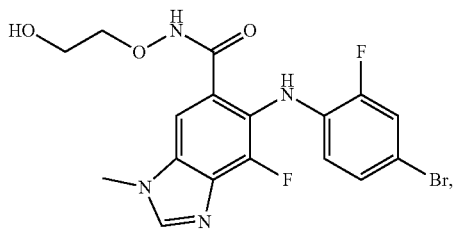

Compound A the process including the steps of:

a) dissolving Compound A in a solution comprising (i.) a solvent system comprising an ether and optionally an alcohol, and (ii.) water to provide a solution;

b) adding a seed crystal suspension to the solution to provide a suspension mixture;

c) cooling the suspension mixture to provide a cooled suspension mixture;

d) adding water to the cooled suspension mixture to provide a treated mixture; and e) cooling the treated mixture, to provide the crystallized 6-(4-bromo-2-fluorophenylamino)-7-fluoro-3-methyl-3H-benzoimidazole-5-carboxylic acid (2-hydroxyethyoxy)-amide.

In accordance with step a) of this aspect of the present invention, Compound A is dissolved in a solution comprising (i.) a solvent system comprising an ether and optionally an alcohol, and (ii.) water. It is understood that step a) may be performed by either: (a) adding Compound A to a solution comprising (i.) a solvent system comprising an ether and optionally an alcohol, and (ii.) water, or (b) adding each component of the solution to Compound A.

Suitable ethers include THF.

In accordance with the present invention, the solution of step a) does not require inclusion of an alcohol. A solution comprising both an ether and an alcohol, however, is preferred. Suitable alcohols include, but are not limited to methanol, ethanol, and isopropanol. Preferably, the alcohol is methanol.

In one embodiment, Compound A is dissolved in a solution consisting of the solvent THF and water.

In one embodiment, Compound A is dissolved in a solution comprising or consisting of (i.) a solvent system including both an ether and an alcohol, and (ii.) water. Preferred, the solution comprises a solvent system including includes an alcohol and THF, and water.

In a preferred embodiment, Compound A is dissolved in a solution consisting of (i.) a solvent system consisting of methanol and THF, and (ii.) water.

The dissolution of Compound A in the solution of step a) is facilitated by heating the mixture of Compound A and the solution comprising (i.) a solvent system comprising an ether and an alcohol, and (ii.) water to an internal temperature of about 52-56° C. prior to addition of the seed crystal suspension.

In one aspect, the mixture of Compound A and the solution comprising (i.) a solvent system comprising an ether and an alcohol, and (ii.) water is heated to an internal temperature of about 53-55° C.

The seed crystal suspension is added to the solution in step b) to provide a suspension mixture. The solution is advantageously cooled (i.) after heating the mixture of Compound A and the solution comprising (i.) a solvent system comprising an ether and an alcohol, and (ii.) water to an internal temperature of about 52-56° C. and (ii.) before addition of the seed crystal suspension.

In one aspect, water is added to the suspension mixture to provide a treated mixture. In another aspect, the suspension mixture is cooled to a temperature of about 30-50° C. before water is added. In a preferred embodiment, the suspension mixture is cooled to a temperature of about 47-48° C. before water is added.

As discussed above, the crystallization process makes use of anti-solvent cooling system. In step d), water is added to the suspension or the cooled suspension mixture to provide a treated mixture. Water, which in general acts as an anti-solvent (solubility <0.01% over a wide temperature range), also unexpectedly acts as a solvent for Compound A when part of the water/methanol/tetrahydrofuran solvent system. Thus, adding water unexpectedly has the effect of significantly increasing the solubility of Compound A. Using this process, it is found that at 65° C., the maximum solubility of Compound A is reached with a mixture of water (24%), methanol (38%), and tetrahydrofuran (38%), with solubility of Compound A decreasing with further addition of water.

The water can be added over a period of 5 to 35 hours, such that the water does not exceed 70% w/w, preferably 65% (w/w), of the solvent system. In one embodiment, the water is added over a period of 10-25 hours, preferably 25 hours. In another embodiment, the water is added over a period of 25 hours such that 33% is added within 15 hours, and 66% is added within 10 hours.

In another aspect, the components in the solvent system upon completion of the addition of water to the suspension or the cooled suspension mixture have a final ratio of alcohol/ether/water in the range between 40/40/20 and 15/15/70 w/w, wherein w/w is referring to the weight percentage of each component relative to the other components of the solvent/antisolvent system. In a preferred embodiment, the final ratio of alcohol/ether/water is approximately 20/20/60 w/w (20/20/60 w/w).

In step e), crystallized Compound A is finally obtained by cooling the treated mixture. The treated mixture is advantageously cooled over a period of 5 to 25 hours. In one aspect, the treated mixture is cooled over a period of 8 to 15 hours, 8 to 12 hours or 9 to 11 hours. In a preferred embodiment, the treated mixture is cooled over a period of approximately 10 hours. The treated mixture is advantageously cooled to an internal temperature of about 1-10° C., preferably about 3-5° C. In a preferred embodiment, the treated mixture is cooled to an internal temperature of about 3-5° C. over a period of approximately 9-11 hours.

After crystallized Compound A is filtered, it can be dried, for example, under vacuum, or in a vacuum oven.

In a further embodiment, the crystallized Compound A provided in step e) in the inventive process above may be subsequently milled. Suitable milling techniques would be known to one of ordinary skill and would include, but not be limited to, pin-milling or jet-milling.

Smaller primary particles often lead to higher agglomeration. However, after milling, crystallized Compound A unexpectedly showed a reduced stickiness, even after storage times of more than three months.

In one further aspect, there is provided is a process for preparing a crystallized form of Compound A comprising the steps of:

a) reacting a compound of Formula (I):

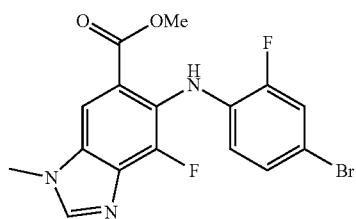

Formula (I)

with a suitable base to form an intermediate; and b) reacting said intermediate with a compound of Formula (II):

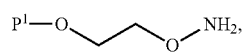

Formula (II)

to provide a compound of Formula (III):

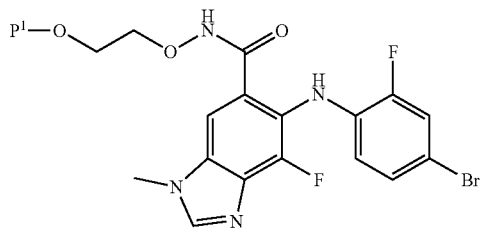

Formula (III)

or a hydrate thereof, wherein $P^1$ is a protecting group;

c) dissolving said compound of Formula (III) or a hydrate thereof in a suitable solvent or solvent system;

d) deprotecting said compound of Formula (III) or a hydrate thereof with a suitable deprotecting reagent, wherein $P^1$ in each occurrence may be the same or different, and is a suitable protecting group, to provide Compound A;

e) dissolving Compound A in a solution comprising (i.) a solvent system comprising an ether and optionally an alcohol, and (ii.) water to provide a solution;

f) adding a seed crystal suspension to the solution to provide a suspension mixture;

g) adding water to the suspension mixture to provide a treated mixture; and h) cooling the treated mixture, to provide the crystallized 6-(4-bromo-2-fluorophenylamino)-7-fluoro-3-methyl-3H-benzoimidazole-5-carboxylic acid (2-hydroxyethyoxy)-amide.

In another aspect, there is provided is a process for preparing a crystallized form of Compound A comprising the steps of:

a) reacting a compound of Formula (I):

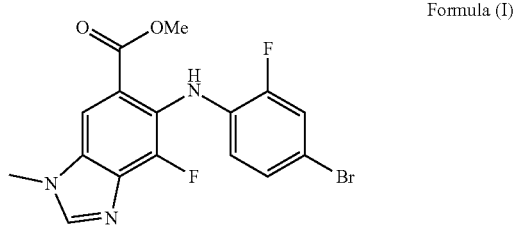 [SMILES: COC(=O)c1cc2c(ncn2C)c(F)c1Nc1ccc(Br)cc1F]

Formula (I)

with a suitable base to form an intermediate; and b) reacting said intermediate with a compound of Formula (II):

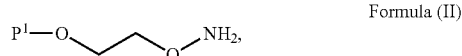

Formula (II)

to provide a compound of Formula (III):

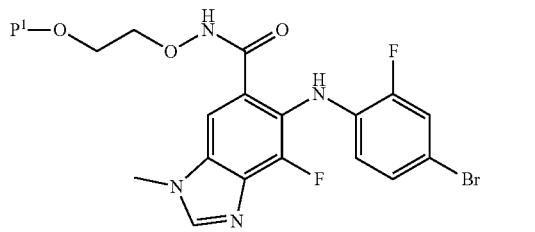

Formula (III)

or a hydrate thereof, wherein $P^1$ is a protecting group;

c) dissolving said compound of Formula (III) or a hydrate thereof in a suitable solvent or solvent system;

d) deprotecting said compound of Formula (III) or a hydrate thereof with a suitable deprotecting reagent, wherein $P^1$ in each occurrence may be the same or different, and is a suitable protecting group, to provide Compound A, e) dissolving Compound A in a solution comprising (i.) a solvent system comprising an ether and optionally an alcohol, and (ii.) water to provide a solution;

f) adding a seed crystal suspension to the solution to provide a suspension mixture; cooling the suspension mixture to provide a cooled suspension mixture;

g) adding water to the cooled suspension mixture to provide a treated mixture; and h) cooling the treated mixture, to provide the crystallized 6-(4-bromo-2-fluorophenylamino)-7-fluoro-3-methyl-3H-benzoimidazole-5-carboxylic acid (2-hydroxyethyoxy)-amide.

The process of step a), in which the compound of Formula (I) is reacted with a suitable base to produce an intermediate. Examples of suitable bases for the foregoing reaction include, but are not limited to, sodium hydroxide, potassium hydroxide, caesium hydroxide, lithium hydroxide, potassium trimethylsilanolate, lithium trimethylsilanolate, and sodium trimethylsilanolate. In a preferred embodiment, the suitable base is potassium trimethylsilanolate. In another preferred embodiment, the suitable base is sodium hydroxide.

The process of step a), in which a compound of Formula (I) is reacted with a suitable base, may be performed in any suitable solvent or solvent system. Suitable solvents include polar aprotic solvents such as acetone, acetonitrile, N,N-dimethylformamide, dimethylsulfoxide, ethyl acetate, tetrahydrofuran, 2-methyl-tetrahydrofuran, and 1,4-dioxane. Suitable solvent systems include any combination of suitable solvents. In a preferred embodiment, the reaction is performed in a mixture of N,N-dimethylformamide and THF. Suitable solvent systems can also include one or more suitable solvents in combination with water. In one particular embodiment, the reaction is performed in a mixture of N,N-dimethylformamide and water.

In one embodiment of the process, steps a) and b) are carried out as a "one-pot" synthesis as described above. In one embodiment, the intermediate of step a) is intermediate 1. In another embodiment, step a) comprises reacting the compound of Formula (I) with the suitable base to form Intermediate 1, and step b) comprises reacting Intermediate 1 with the compound of Formula (II) to form the compound of Formula (III), or a hydrate thereof. In one embodiment, Intermediate 1 is a solution comprising solvents selected from the group consisting of DMF and THF.

In another embodiment of the process, steps a) and b) are carried out with isolation of the intermediate of step a) prior to the reaction of step b) as described above. In one embodiment, the intermediate of step a) is a compound of Formula (V). In another embodiment, the process comprises isolating the intermediate (e.g., the compound of Formula (V)) from the reaction mixture of step a) prior to step b). In one embodiment, the process comprises crystalizing and collecting the intermediate (e.g., the compound of Formula (V)) from the reaction mixture of step a) prior to step b). In one embodiment, the intermediate is crystalized and collected by filtration.

In another embodiment of the process wherein the intermediate of step a) is isolated from the reaction mixture of step a) prior to the reaction of step b), step a) comprises reacting the compound of Formula (I) with the suitable base to form an intermediate of Formula (V), and isolating the intermediate from the reaction mixture; and step b) comprises reacting the intermediate of Formula (V) with the compound of Formula (II) to form the compound of Formula (III), or a hydrate thereof. In one particular embodiment, step a) comprises reacting the compound of Formula (I) with the suitable base followed by reacting with an acid to form the intermediate of Formula (V), and isolating the intermediate of Formula (V) from the reaction mixture; and step b) comprises reacting the intermediate of Formula (V) with the compound of Formula (II) to form the compound of Formula (III), or a hydrate thereof. In one embodiment, the acid is hydrochloric acid.

Suitable protecting groups and deprotecting reagents of steps b) and d) are provided above, and hereby incorporated by reference in its entirety.

The process of step b), in which the intermediate from step a) is reacted with a compound of Formula (II), may be performed in the presence of any coupling agent and a proton source. Suitable proton sources include, but are not limited to, imidazole hydrochloride, pyridinium hydrochloride, triethylamine hydrochloride, N-methylmorpholine hydrochloride, and sulfonic acids such as e.g., methanesulfonic acid, and preferably imidazole hydrochloride. Suitable coupling agents include, but are not limited to, 1,1'-carbonyldiimidazole, isobutylchloroformate, pivaloyl chloride, oxalyl chloride, thionyl chloride, 1-propanephosphonic acid cyclic anhydride, and 1-(3-dimethylaminopropyl)-3-ethyl-carbodiimide hydrochloride (EDCI), and preferably 1,1'-carbonyldiimidazole. In the preferred embodiment of the present invention, the process of step b) is performed in the presence of the coupling agent 1,1'-carbonyldiimidazole and the proton source imidazole hydrochloride. It is within the knowledge of one of ordinary skill in the art to optimize the process of the present invention for coupling agents other than 1,1'-carbonyldiimidazole and proton sources other than imidazole hydrochloride.

It is understood that, in accordance with the present invention, a base may be added to the acidic reaction mixture formed in deprotection step d) to reach a pH in the range of 5-9. Preferably, a base is added to neutralize the acidic reaction mixture formed in deprotection step d) to pH=approximately 8-8.5. Examples of suitable bases include, but are not limited to, potassium hydroxide, sodium hydroxide, lithium hydroxide and ammonium hydroxide. Preferably, the additional base is potassium hydroxide.

In accordance with step e) of this aspect of the present invention, Compound A is dissolved in a solution comprising (i.) a solvent system comprising an ether and optionally an alcohol, and (ii.) water. It is understood that step e) may be performed by either: (a) adding Compound A to a pre-mixed solution comprising (i.) a solvent system comprising an ether and optionally an alcohol, and (ii.) water, or (b) adding each component of the solution to Compound A.

Suitable Ethers Include THF.

In accordance with the present invention, the solution of step e) does not require inclusion of an alcohol. A solution comprising both an ether and an alcohol, however, is preferred. Suitable alcohols include, but are not limited to methanol, ethanol, and isopropanol. Preferably, the alcohol is methanol.

In a preferred embodiment, Compound A is dissolved in a solution consisting of (i.) a solvent system consisting of methanol and THF, and (ii.) water.

The dissolution of Compound A in the solution of step e) is facilitated by heating the mixture of Compound A and the solution comprising (i.) a solvent system comprising an ether and an alcohol, and (ii.) water to an internal temperature of about 52-56° C. prior to addition of the seed crystal suspension. In one aspect, the mixture of Compound A and the solution comprising (i.) a solvent system comprising an ether and an alcohol, and (ii.) water is heated to an internal temperature of about 53-55° C.

The seed crystal suspension is added to the solution in step f) to provide a suspension mixture. The solution is advantageously cooled (i.) after heating the mixture of Compound A and the solution comprising (i.) a solvent system comprising an ether and an alcohol, and (ii.) water to an internal temperature of about 52-56° C. and (ii.) before addition of the seed crystal suspension.

In one aspect, water is added to the suspension mixture to provide a treated mixture. In another aspect, the suspension mixture is cooled to a temperature of about 30-50° C. before water is added. In a preferred embodiment, the suspension mixture is cooled to a temperature of about 47-48° C. before water is added.

In step g), the water can be added over a period of 5 to 35 hours, such that the water does not exceed 70% w/w, preferably 65% (w/w), of the solvent system. In one embodiment, the water is added over a period of 10-25 hours, preferably 25 hours. In another embodiment, the water is added over a period of 25 hours such that 33% is added within 15 hours, and 66% is added within 10 hours.

In another aspect, the components in the solvent system upon completion of the addition of water to the suspension or the cooled suspension mixture have a final ratio of alcohol/ether/water in the range between 40/40/20 and 15/15/70 w/w, wherein w/w is referring to the weight percentage of each component relative to the other components of the solvent/antisolvent system. In a preferred embodiment, the final ratio of alcohol/ether/water is approximately 20/20/60 w/w (20/20/60 w/w).

In step h), crystallized Compound A is finally obtained by cooling the treated mixture. The treated mixture is advantageously cooled over a period of 5 to 25 hours. In one aspect, the treated mixture is cooled over a period of 8 to 15 hours, 8 to 12 hours or 9 to 11 hours. In a preferred embodiment, the treated mixture is cooled over a period of approximately 10 hours. The treated mixture is advantageously cooled to an internal temperature of about 1-10° C., preferably about 3-5° C. In a preferred embodiment, the treated mixture is cooled to an internal temperature of about 3-5° C. over a period of approximately 9-11 hours. After crystallized Compound A is filtered, it can be dried, for example, under vacuum, or in a vacuum oven.

Crystallized Compound A produced by the inventive process can be further milled (e.g., jet milling or pin milling).

In a further aspect, there is provided a crystallized 6-(4-bromo-2-fluorophenylamino)-7-fluoro-3-methyl-3H-benzoimidazole-5-carboxylic acid (2-hydroxyethyoxy)-amide prepared in accordance with the process described herein above, which is hereby incorporated by reference in its entirety. It is understood that the crystallized Compound A includes the drug substance prepared with or without further milling.

In another aspect, there is provided a compound of formula (I):

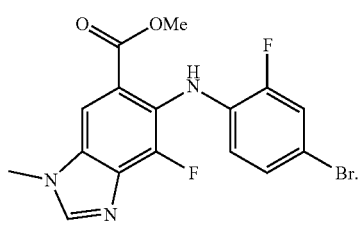

Formula (I)

Said compound of formula (I) is useful as an intermediate compound for the synthesis of Compound A in accordance with the present invention.

In another aspect, provided herein is a compound of Formula (V):

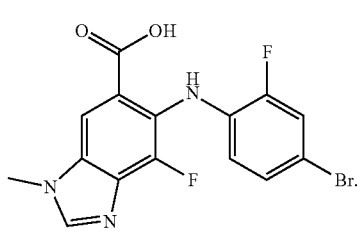

Formula (V)

Said compound of Formula (V) is useful as an intermediate compound for the synthesis of Compound A in accordance with the present invention.

In another aspect, there is provided a compound of formula (IV):

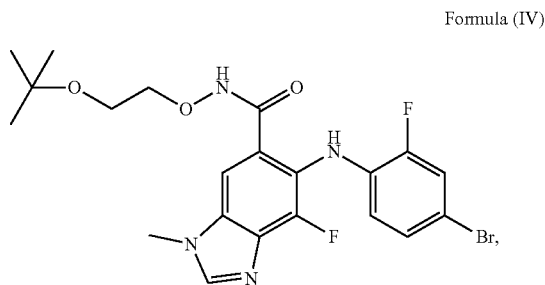 [SMILES: Cn1cnc2c(F)c(Nc3ccc(Br)cc3F)c(C(=O)NOCCOC(C)(C)C)cc21]

Formula (IV)

or a hydrate thereof. In a preferred embodiment, the compound of formula (IV) is in the form of its monohydrate. Said compound of formula (IV), including the monohydrate thereof, is useful as an intermediate compound for the synthesis of Compound A in accordance with the present invention.

Pharmaceutical Compositions Comprising Crystallized Compound a

In another aspect, there is provided a pharmaceutical composition comprising crystallized Compound A and at least one pharmaceutically acceptable carrier or excipient. The pharmaceutical composition comprises crystallized Compound A, at least one sugar, and at least one cellulose-derivative excipient. The composition is particularly useful for the treatment of cancer in a subject in need thereof, preferably humans.

In the pharmaceutical compositions of the present invention, the crystallized Compound A is in a crystal form produced by the crystallization process described above, with or without the milling step. In one embodiment of the pharmaceutical composition provided herein, the pharmaceutical composition comprises about 5-35% crystallized Compound A by weight of composition. In a further embodiment, the pharmaceutical composition comprises about 5-11% crystallized Compound A by weight of composition. In another preferred embodiment, the pharmaceutical composition comprises about 6.25% crystallized Compound A by weight of composition. In another preferred embodiment, the pharmaceutical composition comprises about 10% crystallized Compound A by weight of composition.

In another embodiment, the pharmaceutical composition comprises approximately 15 mg or 45 mg crystallized Compound A.

Suitable sugars for use in the pharmaceutical compositions include, but are not limited to, lactose (e.g., spray-dried lactose, lactose monohydrate), maltose, fructose, galactose, confectioner's sugar, compressible sugar, dextrates, dextrin, dextrose, mannitol, Nu-Tab, Di-Pac, Emdex, and sucrose. In a preferred embodiment, the sugar used in the pharmaceutical composition is lactose, particularly lactose monohydrate.

In one embodiment of the pharmaceutical composition provided herein, the pharmaceutical composition comprises about 30-70% of at least one sugar by weight of composition. In a further embodiment, the pharmaceutical composition comprises about 50-60% of lactose by weight of composition. In a further embodiment, the pharmaceutical composition comprises about 50-60% of lactose monohydrate by weight of composition. In a preferred embodiment, the pharmaceutical composition comprises about 55-56% of lactose monohydrate by weight of composition.

Suitable cellulose-derivative excipients include, but are not limited to, microcrystalline cellulose, microfine cellulose, powdered cellulose, methyl cellulose, hydroxyethyl cellulose, hydroxymethyl cellulose, hydroxypropyl cellulose, and hydroxypropyl methylcellulose. In a preferred embodiment, the cellulose-based excipient is microcrystalline cellulose.

In one embodiment of the pharmaceutical composition provided herein, the pharmaceutical composition comprises about 20-40% cellulose-derivative excipient by weight of composition. In a further embodiment, the pharmaceutical composition comprises about 20-40% microcrystalline cellulose by weight of composition. In a further embodiment, the pharmaceutical composition comprises about 30-40% microcrystalline cellulose by weight of composition. In a preferred embodiment, the pharmaceutical composition comprises about 30-36% microcrystalline cellulose by weight of composition.

The pharmaceutical composition can, for example, be in a form suitable for oral administration in a dosage unit form, such as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition can be in unit dosage forms suitable for single administration of precise dosages. It will be appreciated that the unit content of a combination partner contained in an individual dose of each dosage form need not in itself constitute an effective amount since the necessary effective amount may be reached by administration of a plurality of dosage units.

Methods of preparing various pharmaceutical compositions with a specific amount of active compound are known, or will be apparent, to those skilled in this art. For examples, see *Remington's Pharmaceutical Sciences*, Mack Publishing Company, Ester, Pa., 15$^{th}$ Edition (1975). If not indicated otherwise, the formulation of the present invention is prepared in a manner known per se, for example by means of various conventional mixing, comminution, direct compression, granulating, sugar-coating, dissolving, lyophilizing processes, or fabrication techniques readily apparent to those skilled in the art. Solid compositions of a similar type may also be employed in soft and hard filled gelatin capsules. In a preferred embodiment, the pharmaceutical composition of the present invention is prepared by direct compression.

As described below, the pharmaceutical composition can comprise additional excipients or carriers, including but not limited to disintegrants, lubricants, glidants, binders, stabilizers, and fillers, diluents, colorants, flavours and preservatives. One of ordinary skill in the art may select one or more of the aforementioned carriers with respect to the particular desired properties of the dosage form by routine experimentation and without any undue burden. The amount of each carriers used may vary within ranges conventional in the art. The following references which are all hereby incorporated by reference disclose techniques and excipients used to formulate oral dosage forms. See *The Handbook of Pharmaceutical Excipients*, 4$^{th}$ edition, Rowe et al., Eds., American Pharmaceuticals Association (2003); and *Remington: the Science and Practice of Pharmacy*, 20$^{th}$ edition, Gennaro, Ed., Lippincott Williams & Wilkins (2003). These optional additional conventional carriers may be incorporated into the oral dosage form either by incorporating the one or more conventional carriers into the initial mixture or added during the mixing phases.

Examples of pharmaceutically acceptable disintegrants include, but are not limited to, starches; clays; celluloses; alginates; gums; cross-linked polymers, e.g., cross-linked polyvinyl pyrrolidone or crospovidone, e.g., POLYPLASDONE XL from International Specialty Products (Wayne, N.J.); cross-linked sodium carboxymethylcellulose or croscarmellose sodium (e.g., AC-DI-SOL from FMC); and cross-linked calcium carboxymethylcellulose; soy polysaccharides; and guar gum. The disintegrant may be present in an amount from about 0% to about 10% by weight of the composition. In one embodiment, the disintegrant is present in an amount from about 0.1-5%, or about 1-3%, or about 1.5-2.5% by weight of composition.

In one embodiment, the pharmaceutical composition of the present invention includes the disintegrant croscarmellose sodium. In a further embodiment, the pharmaceutical composition of the present invention includes about 2% croscarmellose sodium by weight of composition.

Examples of pharmaceutically acceptable lubricants and pharmaceutically acceptable glidants include, but are not limited to, colloidal silicon dioxide/colloidal anhydrous silica (e.g., Aerosil 200®), magnesium trisilicate, starches, talc, tribasic calcium phosphate, magnesium stearate, aluminum stearate, calcium stearate, magnesium carbonate, magnesium oxide, polyethylene glycol, powdered cellulose and microcrystalline cellulose. The lubricant may be present in an amount from about 0% to about 10% by weight of the composition. In one embodiment, the lubricant may be present in an amount from about 0.1-1.5%, about 0.1-1%, or about 0.5-0.9% by weight of composition. The glidant may be present in an amount from about 0.1-10%, about 0.1-5%, or about 0.1-1% by weight of composition.

In one embodiment, the pharmaceutical composition of the present invention includes the glidant colloidal silicon dioxide/colloidal anhydrous silica. In a further embodiment, the pharmaceutical composition of the present invention includes about 0.25% (by weight of composition) colloidal silicon dioxide/colloidal anhydrous silica.

In another embodiment, the pharmaceutical composition of the present invention includes the lubricant magnesium stearate. In a further embodiment, the pharmaceutical composition of the present invention includes about 0.75% magnesium stearate by weight of composition.

In another embodiment, the pharmaceutical composition of the present invention includes colloidal silicon dioxide/colloidal anhydrous silica and magnesium stearate. In a further embodiment, the pharmaceutical composition of the present invention includes about 0.25% colloidal silicon dioxide/colloidal anhydrous silica by weight of composition and about 0.75% magnesium stearate by weight of composition.

Examples of pharmaceutically acceptable binders include, but are not limited to, starches; celluloses and derivatives thereof, for example, microcrystalline cellulose, e.g., AVICEL PH from FMC (Philadelphia, Pa.), hydroxypropyl cellulose hydroxylethyl cellulose and hydroxylpropylmethyl cellulose METHOCEL from Dow Chemical Corp. (Midland, Mich.); sucrose; dextrose; corn syrup; polysaccharides; and gelatin. The binder may be present in an amount from about 0-50%, or about 2-20% by weight of the composition.

Examples of pharmaceutically acceptable diluents include, but are not limited to, confectioner's sugar, compressible sugar, dextrates, dextrin, dextrose, lactose, mannitol, microcrystalline cellulose, powdered cellulose, sorbitol, sucrose and talc. The diluent, e.g., may be present in an amount from about 0-80%, or about 0-50%, or about 1-40% or about 1-10% by weight of the composition.

In a particular embodiment, the pharmaceutical composition further comprises one or more of croscarmellose sodium, magnesium stearate, and silicon dioxide.

When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

In a particular embodiment, the pharmaceutical composition comprises about 5-11% crystallized Compound A by weight of composition, about 55-56% lactose monohydrate by weight of composition, and about 30-36% microcrystalline cellulose by weight of composition.

In another embodiment, the composition comprises about 5-11% of crystallized 6-(4-bromo-2-fluorophenylamino)-7-fluoro-3-methyl-3H-benzoimidazole-5-carboxylic acid (2-hydroxyethyoxy)-amide, about 55-56% of lactose monohydrate, about 30-36% of microcrystalline cellulose, by weight of composition, about 1.5-2.5% of croscarmellose sodium, about 0.5-0.9% of magnesium stearate, and about 0.1-1% percent colloidal silicon dioxide/colloidal anhydrous silica, by weight of composition.

In another embodiment, the composition comprises about 5-11% crystallized Compound A by weight of composition, about 55-56% lactose monohydrate by weight of composition, about 30-36% microcrystalline cellulose by weight of composition, about 2% croscarmellose sodium by weight of composition, about 0.75 percent magnesium stearate by weight of composition, and about 0.25 percent colloidal silicon dioxide/colloidal anhydrous silica by weight of composition.

In another embodiment of the pharmaceutical composition, the pharmaceutical composition is in tablet form. In still another embodiment, the tablet is a coated tablet.

In one aspect, the pharmaceutical composition of the present invention further comprises at least one additional therapeutic agent. Examples of additional therapeutic agents include, but are not limited to, chemotherapeutic agents or anti-tumor agents, such as mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

In one embodiment, the additional therapeutic agent is selected from the group consisting of paclitaxel or everolimus.

It is understood that the crystallized Compound A and the additional agent may be administered in the same or different dosage unit forms. Further, such combination partners may be administered simultaneously, separately or sequentially.

Methods of Treating Proliferative Disease with Crystallized Compound A

In one aspect, the invention provides a method of treating a proliferative disease, particularly cancer, in a subject, comprising administering to the subject an effective amount of a crystallized 6-(4-bromo-2-fluorophenylamino)-7-fluoro-3-methyl-3H-benzoimidazole-5-carboxylic acid (2-hydroxyethyoxy)-amide ("Compound A"). It is understood that crystallized Compound A is in crystalline form produced by the crystallization process described above.

In a further aspect, the invention provides a method of treating a proliferative disease, particularly cancer, in a subject, comprising administering to the subject an effective amount a pharmaceutical composition comprising crystallized 6-(4-bromo-2-fluorophenylamino)-7-fluoro-3-methyl-3H-benzoimidazole-5-carboxylic acid (2-hydroxyethyoxy)-amide ("Compound A"), at least one sugar, and at least one cellulose-derivative excipient. It is understood that crystallized Compound A is in crystalline form produced by the crystallization process described above.

It is further understood that the present invention includes a method of treating a proliferative disease, particularly cancer, in a subject by administering to a subject an effect amount of a pharmaceutical composition comprising crystallized Compound A as provided in each embodiment set forth above, which is herein incorporated by reference.

In accordance with the method of treatment of the present invention, the crystallized Compound A is administered to a subject in need thereof in a therapeutically effective amount.

Crystallized Compound A may be administered to a suitable subject daily in single or divided doses at an effective dosage in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day.

The crystallized Compound A and/or the pharmaceutical compositions of the present invention may be used for treatment of proliferative diseases which are cancerous or non-cancerous. It is expressly preferred for treatment of cancer.

"Cancer" that can be treated using the pharmaceutical composition provided herein refers to cellular-proliferative disease states, including but not limited to solid or liquid tumors. Examples of cancers suitable for treatment in accordance with the present invention include, but are not limited to, lung cancer, bone cancer, CMML, pancreatic cancer, skin cancer, cancer of the head and neck, melanoma, intrauterine cancer, ovarian cancer, colon cancer, rectal cancer, anal cancer, stomach or gastric cancer, breast cancer, testicular cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, esophageal cancer, cancer of the small intestine, cancer of the endocrine system (e.g., thyroid cancer, parathyroid cancer, or adrenal gland cancer), soft tissue sarcoma, cancer of the urethra, penile cancer, prostate cancer, chronic or acute leukemia, solid tumors of childhood, lymphocytic lymphomas, bladder cancer, cancer of the kidney or ureter (e.g., renal cell carcinoma), carcinoma of the renal pelvis, biliary cancer, brain cancer, bladder cancer, squamous cell, peritoneal cancer, or neoplasms of the central nervous system (e.g., primary CNS lymphoma, spinal axis tumors, brain stem gliomas or pituitary adenomas). In one embodiment, the cancer is a solid tumor. In a particular embodiment, the solid tumor is metastatic or unresectable.

In one embodiment, the cancer is cancer such as brain, lung, squamous cell, bladder, gastric, pancreatic, breast, head, neck, renal, kidney, ovarian, prostate, colon, rectal, esophageal, testicular, gynecological or thyroid cancer.

In one embodiment, the cancer is lung cancer, squamous cell cancer, pancreatic cancer, breast cancer, head cancer, neck cancer, colon cancer, rectal cancer or melanoma.

In a particular embodiment, provided herein is a method of treating melanoma, pancreatic cancer, ovarian cancer, carcinoma of the fallopian tubes, peritoneal cancer, biliary cancer, colon cancer, or rectal cancer in a subject in need thereof, comprising administering to the subject the crystallized Compound A or the pharmaceutical composition provided herein.

In another embodiment, the proliferative disease is a non-cancerous proliferative disorder such as benign hyperplasia of the skin (e.g., psoriasis), restenosis, prostate (e.g., benign prostatic hypertrophy (BPH), or Noonan Syndrome. Examples of additional therapeutic agents include, but are not limited to chemotherapeutic agents or anti-tumor agents, such as mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

In one embodiment, the additional therapeutic agent is selected from the group consisting of paclitaxel or everolimus.

It is understood that the crystallized Compound A and the additional agent may be administered in the same or different dosage unit forms. Further, such combination partners may be administered simultaneously, separately or sequentially.

In one aspect, the invention provides the use of crystallized Compound A for the preparation of a medicament suitable for treatment of a proliferative disease, particularly cancer. It is understood that crystallized Compound A is in crystalline form produced by the crystallization process described above. In one embodiment, the proliferative disease is a solid tumor. In a further embodiment, the proliferative disease is a cancer as set forth above.

In another aspect, the invention provides the use of the pharmaceutical composition of the present invention for the preparation of a medicament suitable for treatment of a proliferative disease, particularly cancer. In one embodiment, the proliferative disease is a solid tumor. In a further embodiment, the proliferative disease is a cancer as set forth above.

In a particular embodiment of each aspect, the proliferative disease is selected from melanoma, pancreatic cancer, ovarian cancer, carcinoma of the fallopian tubes, peritoneal cancer, biliary cancer, colon cancer, or rectal cancer.

In one aspect, the invention provides crystallized Compound A for use in the treatment of a proliferative disease, particularly cancer. It is understood that crystalline Compound A is in crystalline form produced by the crystallization process described above. In one embodiment, the proliferative disease is a solid tumor. In a further embodiment, the proliferative disease is a cancer as set forth above.

In another aspect, the invention provides the pharmaceutical composition of the present invention, as described above and incorporated herein by reference, for use in the treatment of a proliferative disease, particularly cancer. In one embodiment, the proliferative disease is a solid tumor. In a further embodiment, the proliferative disease is a cancer as set forth above.

In a particular embodiment of each aspect, the proliferative disease is selected from melanoma, pancreatic cancer, ovarian cancer, carcinoma of the fallopian tubes, peritoneal cancer, biliary cancer, colon cancer, or rectal cancer.

The invention is illustrated further by the following examples which are not to be construed as limiting the invention in scope or spirit to the specific procedures described in them.

The starting materials and various intermediates may be obtained from commercial sources, prepared from commercially available organic compounds, or prepared using well known synthetic methods.

Representative examples of the methods and formulations of the invention are set forth below. These examples are not, however, intended to limit the scope of the invention in any way.

EXAMPLES

Abbreviations

The following abbreviations are used in the text:
CDI—1,1'-carbonyldiimidazole
DMF—N,N-dimethylformamide
KOTMS—potassiumtrimethylsilanolate
THF—tetrahydrofuran
EKNS—activated charcoal
CEFOK—microcrystalline cellulose Example 1

Preparation of 6-(4-Bromo-2-fluorophenylamino)-7-fluoro-3-methyl-3H-benzoimidazole-5-carboxylic acid methyl ester

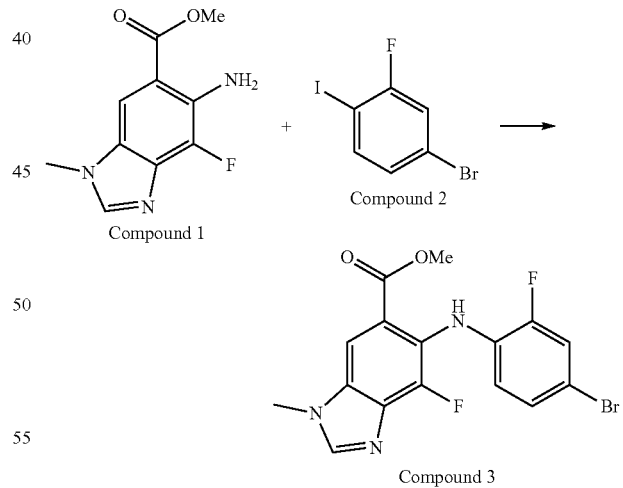

In an inertized ($N_2$) reaction vessel at internal temperature 20° C. and under exclusion of humidity and air, Compound 1 (1.0 eq.) and Compound 2 (1.2 eq.) are reacted in the presence of cesium carbonate (2.4 eq.), tris(dibenzylidenaceton) dipalladium(0) (0.035 eq.) and Xantphos (0.07 eq.) in a mixture of toluene and 1,4-dioxane at internal temperature of 99° C. After 8 hours, the mixture is cooled to internal temperature of 60° C.

Subsequently, dimethylformamide (DMF), filter aid (CEFOK) and activated charcoal (EKNS) are added, and the mixture is stirred and cooled to internal temperature of 35° C. The solids are filtered off and washed with a mixture of dimethylformamide and toluene. To the filtrate, which contains the product Compound 3, is introduced at internal temperature of 25° C. hydrogen chloride gas (CLC) whereupon the HCl salt of Compound 3 crystallizes. The palladium residue mainly remains in solution. After warming to 60° C. and cooling to 0° C., the solids are filtered using a centrifuge and are washed with a mixture of toluene and dimethylformamide.

The damp Compound 3 HCl salt is charged to a reactor (equipped with pH probe) together with dimethylformamide and is heated to 60° C. By adding a 4 wt % of aqueous tripotassium phosphate solution, the pH is adjusted to a pH range of 6.8-7.6 (with a target of pH 7.2) while Compound 3 crystallizes as free base. After cooling to 22° C. and stirring, the solids are filtered using a centrifuge and are washed with drinking water. The moist solids are dried at 50° C. under vacuum to give dry, crude Compound 3.

In order to remove residual palladium, dry, crude Compound 3 is dissolved in dimethylformamide at internal temperature of 60° C. and stirred together with Smopex-234 (commercially available from Johnson Matthey) and activated charcoal for 90 minutes. The solids are filtered off at internal temperature of 60° C. and are washed with dimethylformamide. To the filtrate are added drinking water and Compound 3 seed crystals. More drinking water is added while Compound 3 crystallizes. After cooling to internal temperature of 20° C., the solids are filtered using a centrifuge and are washed with a mixture of deionized water and dimethylformamide and with deionized water. The moist solids are dried at 50° C. under vacuum, providing 6-(4-Bromo-2-fluorophenylamino)-7-fluoro-3-methyl-3H-benzoimidazole-5-carboxylic acid methyl ester (Compound 3).

Example 2

Preparation of 6-(4-Bromo-2-fluorophenylamino)-7-fluoro-3-methyl-3H-benzoimidazole-5-carboxylic acid-(2-tert-butoxyethoxy)-amide A. "One-Pot" Synthesis

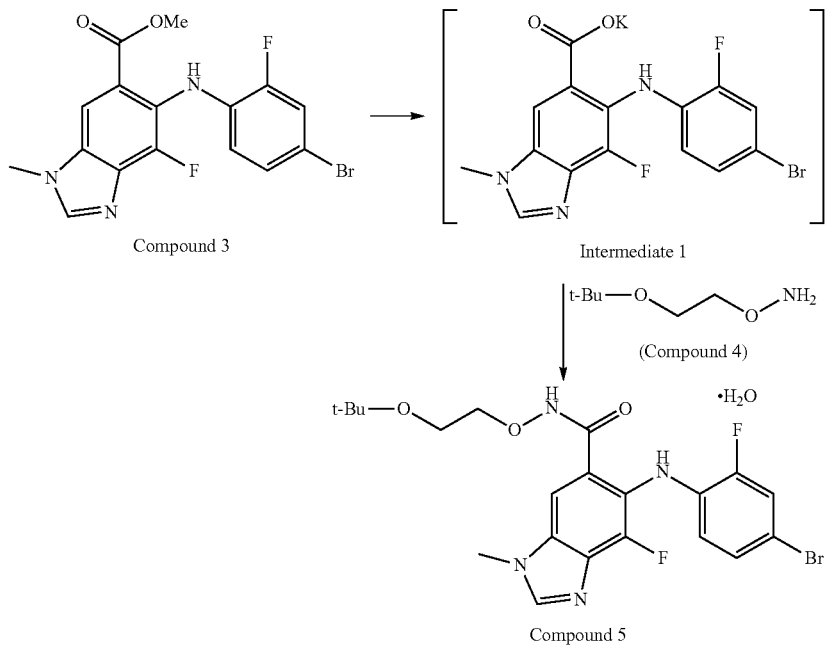

In an inertized reaction vessel at internal temperature 20-25° C. under nitrogen, 6-(4-Bromo-2-fluorophenylamino)-7-fluoro-3-methyl-3H-benzoimidazole-5-carboxylic acid methyl ester (Compound 3, 1.0 eq.) is added to a mixture of DMF and THF. To this slurry, a solution of potassium trimethylsilanolate (1.05 eq.) in THF is added to the mixture at internal temperature of 25° C. over a period of about 40 minutes, and the resulting mixture is stirred for about 1 hour, providing a potassium salt solution of Intermediate 1. A THF/methanol mixture is then sequentially distilled off from the mixture at 85-120° C. during about 2 hours.

The potassium salt solution is then added to a suspension of CDI (1.25 eq.) and imidazole hydrochloride (1.40 eq.) in THF at internal temperature of 25° C. over a period of about 1 hour. The resulting mixture is then stirred for approximately 1 hour at 50° C., and the following imidazolide intermediate is formed:

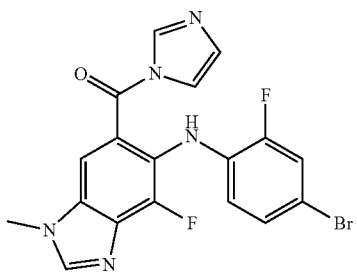 [SMILES: Cn1cnc2c(F)c(Nc3ccc(Br)cc3F)c(C(=O)n3ccnc3)cc21]

The imidazolide intermediate is not further isolated.

Subsequently, 1.2 eq. of O-(2-tert-butoxyethyl)hydroxylamine (Compound 4, CAS No. 1023742-13-3, available from suppliers such as Huhu Technology, Inc.®) is added over a period of about 30 minutes at 50° C. and stirred for 1.5 hours. Demineralized water is then added at 50° C., producing a precipitate. After cooling to 20° C. and stirring for about 3-16 hours, the slurry is filtered off, washed with THF/demineralized water (1:2) in 2 portions and with demineralized water in three portions, and dried at 50° C./<70 mbar for about 17 hours, providing 6-(4-bromo-2-fluorophenylamino)-7-fluoro-3-methyl-3H-benzoimidazole-5-carboxylic acid-(2-tert-butoxyethoxy)-amide (Compound 5) as monohydrate.

B. A Synthesis Method with Isolation of the Intermediate of Step a) from the Reaction Mixture of Step a) Prior to the Reaction of Step b)

Alternatively, 6-(4-bromo-2-fluorophenylamino)-7-fluoro-3-methyl-3H-benzoimidazole-5-carboxylic acid-(2-tert-butoxyethoxy)-amide (Compound 5) can be made by the synthesis method as shown below. Compound 3, which is a methyl ester, is first converted to a carboxylic acid, which is then isolated by a crystallization to form Compound 6. Compound 6 is then coupled with Compound 4 to form Compound 5 as monohydrate. The crystallization step in this method removes starting materials such as Compound 1, process impurities, and the dba ligand from the prior catalyst before the coupling reaction with Compound 4, and at the same time maintains the overall yield of the synthesis.

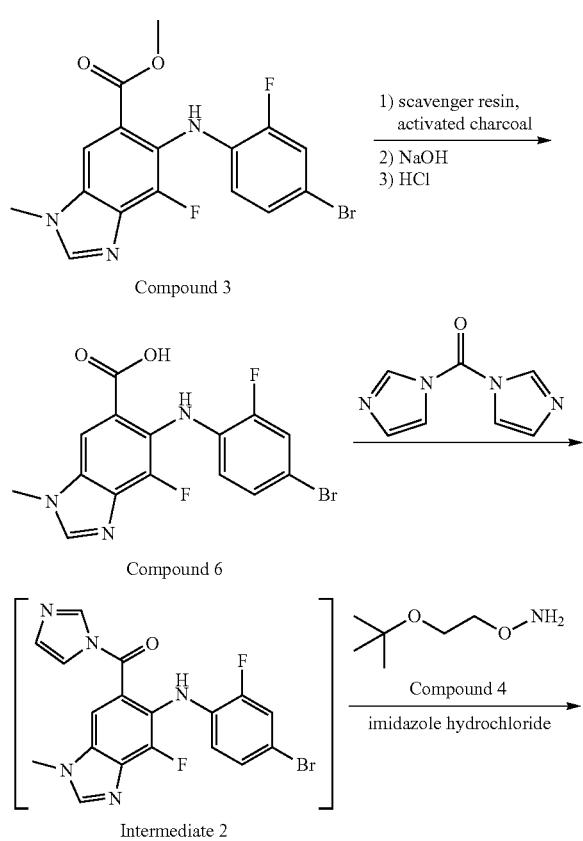

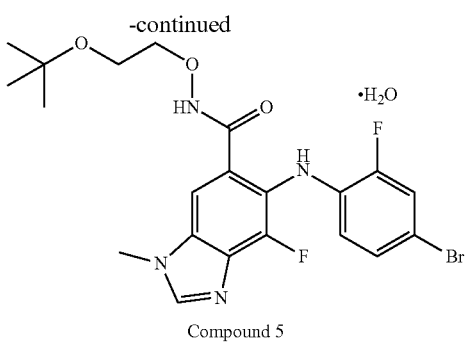

Compound 5

6-(4-Bromo-2-fluorophenylamino)-7-fluoro-3-methyl-3H-benzoimidazole-5-carboxylic acid In an inertized ($N_2$) reaction vessel at internal temperature of 60° C., Compound 3 (1.0 eq.) is dissolved in DMF and stirred with a fiber, which is sold under the trademark SMOPEX 234, and activated charcoal for the removal of palladium to not more than 100 ppm. The fiber and activated charcoal are removed by filtration at 60° C. and washed with DMF.

The filtrate (containing Compound 3) is transferred to a second inertized ($N_2$) reaction vessel and cooled to an internal temperature of 30° C. A thin suspension can form at this point of time. 30% sodium hydroxide (1.1 eq.) and water (for rinsing) are added, and the resulting reaction mixture is vigorously stirred for 3 hours at an internal temperature of 30° C. The methyl ester is saponified. Conversion is checked by an IPC (HPLC). As soon as the IPC criterion is met, a filter aid, which is sold under the trademark HYFLO, is added. The mixture is stirred for 15 minutes and then filtered at 30° C. via a plate filter and polish filter to a third reaction inertized ($N_2$) vessel.

An aqueous HCl solution 7.5% is added to the clear filtrate in the third vessel at an internal temperature of 30° C. until a pH value of 8 is reached. Then the solution is seeded at an internal temperature of 30° C. with Compound 6, and an aqueous HCl solution 7.5% is added under vigorous stirring until a pH value of pH 2.8 is reached. The product gradually crystallizes. The suspension is cooled over 60 min to an internal temperature of 25° C. and water is added. The suspension is stirred for at least 4 hours at an internal temperature of 25° C.

The resulting solid is collected by centrifugation or filtration. The filter cake is first washed with DMF/water 1:1 (w/w) and then with water, discharged and dried in a vacuum at 50° C. The water content is controlled by IPC. The crystalline product Compound 6 is discharged as soon as the IPC criterion is met.

6-(4-Bromo-2-fluorophenylamino)-7-fluoro-3-methyl-3H-benzoimidazole-5-carboxylic acid-(2-tert-butoxyethoxy)-amide An inertized ($N_2$) reaction vessel is charged with Compound 6 (1.0 eq.), DMF, and THF at room temperature. The suspension is heated to 25° C. under stirring with flow of nitrogen. After CDI (1.13 eq.) is added, the suspension can get thinner and slight evolution of gases can be observed. After the suspension finally becomes a solution, it is then monitored by IPC (HPLC).

As soon as the IPC (HPLC) criterion is met, the reaction mixture is heated to 50° C. over 20 minutes and imidazole hydrochloride (0.3 eq.) is added, forming a solution of Intermediate 2.

To the solution of Intermediate 2, Compound 4 (1.3 eq.) is added over 60 minutes at internal temperature of 50° C. under stirring at a speed of 300 rpm with flow of nitrogen. As soon as the IPC (HPLC) criterion is met, the mixture is cooled to 20-25° C. over 30 minutes. The mixture is then stored at ambient temperature overnight under nitrogen without stirring. DMF is added to the mixture followed by heating it to 50° C. over 30 minutes. Complete conversion of Intermediate 2 to Compound 5 is confirmed by IPC (HPLC).

Water is added to the mixture at internal temperature of 50° C. over 20 minutes. Then the solution is seeded with Compound 5. After stirring at 50° C. for 60 minutes, more water is added to the suspension at 50° C. over 90 minutes. After vigorous stirring, the suspension is cooled to 20° C. over 2 hours and filtered. The filter cake is washed twice with THF/water (v/v: 1:2) at 20° C., and twice with water at 20° C. Finally, the filter cake is dried at 50° C. under vacuum to provide 6-(4-bromo-2-fluorophenylamino)-7-fluoro-3-methyl-3H-benzoimidazole-5-carboxylic acid-(2-tert-butoxyethoxy)-amide (Compound 5) as monohydrate.

Example 3

Preparation of 6-(4-Bromo-2-fluorophenylamino)-7-fluoro-3-methyl-3H-benzoimidazole-5-carboxylic acid (2-hydroxyethyoxy)-amide (Compound A)

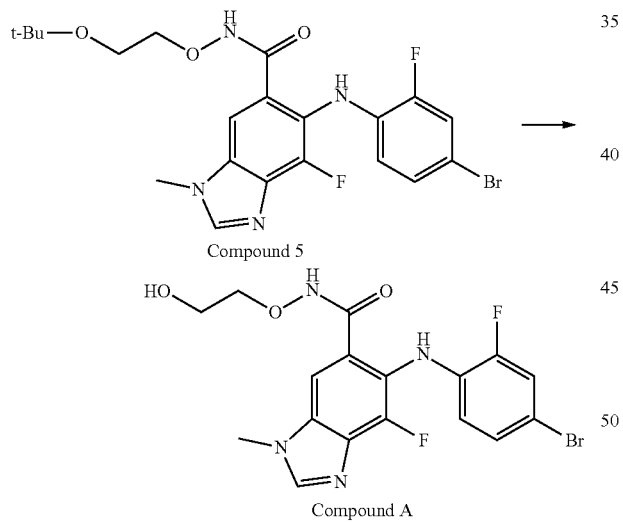

Compound 5

Compound A 6-(4-Bromo-2-fluorophenylamino)-7-fluoro-3-methyl-3H-benzoimidazole-5-carboxylic acid-(2-tert-butoxyethoxy)-amide (Compound 5) monohydrate is added in 3 portions to a premixed solution of Acetonitrile and excess Phosphoric acid (85% aqueous solution) at internal temperature 20-25° C. After stirring for about 15 minutes, the suspension is heated to internal temperature 50-53° C. The suspension is maintained at this temperature for 6 hours, cooled to internal temperature 20-23° C. The mixture is then heated to internal temperature 35-37° C. and diluted with Ethanol-Water (3:1 v/v). EKNS and CEFOK are added, the reaction mixture is stirred approximately 15 minutes and filtered over a funnel coated with CEFOK. The filtrate is cooled to approximately 30° C. 3 N aqueous potassium hydroxide (KOH) is added to the cooled filtrate over a period of 90 minutes until a pH-value of about 8.1 is reached. The suspension is heated to internal temperature 60-63° C., stirred at this temperature for a period of about 2 hours, cooled to 20-23° C. over a period of about 45 minutes, filtered over a funnel, and dried at 50° C. pressure <100 mbar over a period of about 17 hours, providing 6-(4-bromo-2-fluorophenylamino)-7-fluoro-3-methyl-3H-benzoimidazole-5-carboxylic acid (2-hydroxyethyoxy)-amide (Compound A) as a white powder.

Example 4

Preparation of Crystallized 6-(4-bromo-2-fluorophenylamino)-7-fluoro-3-methyl-3H-benzoimidazole-5-carboxylic acid (2-hydroxyethyoxy)-amide (Compound A)

In a dry vessel at room temperature, Compound A is added to a premixed solvent solution of methanol/THF/water (35/35/30 w/w). The suspension is heated to internal temperature 53-55° C., and the resulting solution is hot filtered by deep and membrane filtration (via a paper filter and PTFE membrane) at internal temperature 53-56° C. The clear solution is stirred and cooled to 47-48° C., and the seed crystals suspension (i.e., seed crystals of crystallized Compound A in water, 10% m/m) is added (0.2 to 0.5% of crystallized Compound A expected yield mass). After about 20 minutes, water is slowly added within 25 hours (33.3% within 15 hours and 66.6% within 10 hours with at least 10 minute stirring after addition of water) to obtain a final ratio of methanol/THF/water (20/20/60 w/w). After the water is added, the suspension is cooled down to internal temperature 3-5° C. within 10 hours and stirred for 0.5 hours. The white suspension is filtered over a sinter glass nutsche (75 ml, diameter=6 cm, pore 3) suction filter and washed once with ice cold methanol/THF/water (15/15/70 w/w at 2-4° C.), and two times with ice cold water (2-4° C.). Drying takes place in a vacuum oven dryer at 20° C. for 10 hours, and then at 40° C. for 10 hours, and then at 60° C. for at least 12 hours with pressure <10 mbar, providing crystallized Compound A.

Example 5

Pharmaceutical Composition

Crystallized Compound A is formulated as indicated in Table 1:

TABLE 1

| Formulation | | Form 1 (% by weight) | Form 1 (in mg/unit) | Form 2 (% by weight) | Form 2 (in mg/unit) |
|---|---|---|---|---|---|
| Tablet core | | | | | |
| Crystallized Drug Substance Compound A | Active | 6.25% | 15 | 10.00% | 15.00 |
| Lactose monohydrate | Filler | 55.63% | 133.5 | 55.62% | 83.43 |
| Microcrystalline cellulose | Filler | 35.13% | 84.3 | 31.37% | 47.06 |
| Croscarmellose Sodium | Disintegrant | 2.00% | 4.8 | 2.00% | 3 |

TABLE 1-continued

| Formulation | | Form 1 (% by weight) | Form 1 (in mg/unit) | Form 2 (% by weight) | Form 2 (in mg/unit) |
|---|---|---|---|---|---|
| Magnesium Stearate | Lubricant | 0.75% | 1.8 | 0.75% | 1.13 |
| Colloidal Silicon Dioxide/Silica, colloidal anhydrous (e.g., Aerosil 200 ©) | Glidant | 0.25% | 0.6 | 0.25% | 0.38 |
| TOTAL: Tablet coating | | | 240 | | 150 |
| Tablet core (from above) | | 100% | | 100% | |
| Opadry II (Yellow) ®** | Film coat | 3.50% | 8.4 | 3.50% | 8.4 |
| Sterile water for irrigation*** | Solvent | — | | — | |

*The weight of the drug substance is taken with reference to the dried substance (100%) on the basis of assayed value. The difference in weight is adjusted by the amount of lactose monohydrate.
**The Opadry II is combined with the sterile water to make a 12% w/w Opadry II (85F) film coat suspension, which is then sprayed onto the core tablet.
***Removed during processing Upon mixing of the tablet core components, the pharmaceutical composition is converted into a tablet form by direct compression. The formed tablet may be further coated with the tablet coating provided above.

What is claimed is:

1. A method of treating a cancer is selected from melanoma, pancreatic cancer, ovarian cancer, carcinoma of the fallopian tubes, peritoneal cancer, biliary cancer, colon cancer, or rectal cancer in a patient in need thereof, comprising administering to said mammal a pharmaceutical composition comprising crystallized 6-(4-bromo-2-fluorophenylamino)-7-fluoro-3-methyl-3H-benzoimidazole-5-carboxylic acid (2-hydroxyethyoxy)-amide and a pharmaceutically acceptable carrier or excipient.

2. The method according to claim 1, wherein the cancer is melanoma.

3. The method according to claim 2, wherein said melanoma is BRAFV600 or NRAS-mutant melanoma.

4. The method according to claim 3, wherein the pharmaceutical composition is formulated as a tablet.

5. The method according to claim 4, wherein the pharmaceutical composition comprises approximately 15 mg crystallized 6-(4-bromo-2-fluorophenylamino)-7-fluoro-3-methyl-3H-benzoimidazole-5-carboxylic acid (2-hydroxyethyoxy)-amide.

6. The method according to claim 5, wherein the pharmaceutical composition further comprises lactose monohydrate, microcrystalline cellulose, colloidal silicon dioxide, croscarmellose sodium, and magnesium stearate.

7. The method according to claim 6, wherein said melanoma is NRAS-mutant melanoma.

8. The method according to claim 3, further comprising administering an additional therapeutic agent.

9. The method according to claim 8, wherein the additional therapeutic agent is a chemotherapeutic agent or anti-tumor agent.

10. The method according to claim 9, wherein the pharmaceutical composition comprising crystallized 6-(4-bromo-2-fluorophenylamino)-7-fluoro-3-methyl-3H-benzoimidazole-5-carboxylic acid (2-hydroxyethyoxy)-amide and the additional therapeutic agent are administered separately.

11. The method according to claim 10, wherein said melanoma is BRAFV600 mutant melanoma.

12. The method according to claim 9, wherein the pharmaceutical composition comprising crystallized 6-(4-bromo-2-fluorophenylamino)-7-fluoro-3-methyl-3H-benzoimidazole-5-carboxylic acid (2-hydroxyethyoxy)-amide and the additional therapeutic agent are administered simultaneously.

13. The method according to claim 1, wherein the cancer is colon cancer.

14. The method according to claim 1, wherein the cancer is ovarian cancer.

* * * * *

UNITED STATES PATENT AND TRADEMARK OFFICE
CERTIFICATE OF CORRECTION

PATENT NO. : 9,598,376 B2
APPLICATION NO. : 15/053441
DATED : March 21, 2017
INVENTOR(S) : Krell et al.

Page 1 of 1

It is certified that error appears in the above-identified patent and that said Letters Patent is hereby corrected as shown below:

In the Claims

Column 37, Line 28, in Claim 1 after "cancer" delete "is".

Signed and Sealed this
Twentieth Day of June, 2017

Joseph Matal
*Performing the Functions and Duties of the*
*Under Secretary of Commerce for Intellectual Property and*
*Director of the United States Patent and Trademark Office*